United States Patent
Betlach et al.

(10) Patent No.: US 6,303,767 B1
(45) Date of Patent: Oct. 16, 2001

(54) **NUCLEIC ACIDS ENCODING NARBONOLIDE POLYKETIDE SYNTHASE ENZYMES FROM *STREPTOMYCES NARBONENSIS***

(75) Inventors: Melanie C. Betlach, San Francisco; Robert McDaniel, Palo Alto, both of CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/434,288

(22) Filed: Nov. 5, 1999

Related U.S. Application Data

(63) Continuation-in-part of application No. 09/320,878, filed on May 27, 1999, now Pat. No. 6,117,659.
(60) Provisional application No. 60/107,093, filed on Nov. 5, 1998.

(51) Int. Cl.[7] .................................................... C07H 21/04

(52) U.S. Cl. ...................... 536/23.2; 536/23.1; 435/320.1

(58) Field of Search ................ 536/23.1, 23.2; 435/320.1

(56) References Cited

U.S. PATENT DOCUMENTS

| | | | |
|---|---|---|---|
| 5,614,619 | * 3/1997 | Piepersberg et al. | ............... 536/23.2 |
| 5,712,146 | 1/1998 | Khosla et al. | . |
| 5,824,513 | 10/1998 | Katz et al. | . |
| 5,945,320 | * 8/1999 | Burgett et al. | ........................ 435/183 |

FOREIGN PATENT DOCUMENTS

| | | |
|---|---|---|
| WO 97/23630 | 3/1997 | (WO) . |
| WO 97/22711 | 6/1997 | (WO) . |

OTHER PUBLICATIONS

Xue, Y. et al., "Hydroxylation of macrolactones YC–17 and narbomycin is mediated by the pikc–encoded cytochrome P450 in *Streptomyces venezuelae*," *Chemistry & Biology* (1998), 5:661–667.

Xue, Y. et al., "A gene cluster for macrolide antibiotic biosynthesis in *Streptomyces venezuelae*: Architecture of metabolic diversity," *Proc. Natl. Acad. Sci. USA* (1998), 95:12111–12116.

Cortes et al. An unusually large multifunctional polypeptide in the erythromycin–producing polyketide synthase of *Saccharopolyspora erythraea*. Nature (1990) 348:176–178, Nov. 1990.*

Maezawa et al. Biological conversion of narbonolide to pciromycin, J. of Antibiotics (1973) 26(12): 771–775, 1973.*

* cited by examiner

*Primary Examiner*—Ponnathapu Achutamurthy
*Assistant Examiner*—Kathleen Kerr
(74) *Attorney, Agent, or Firm*—Kevin Kaster; Carolyn Favorito; Kate Murashige

(57) ABSTRACT

Host cells comprising recombinant vectors encoding the narbomycin polyketide synthase and narbomycin modification enzymes from *Streptomyces narbonensis* can be used to produce narbomycin, picromycin, methymycin, and neomethymycin. Recombinant DNA constructs comprising one or more narbomycin polyketide synthase domains, modules, open reading frames, and variants thereof can be used to produce recombinant polyketide synthases and a variety of different polyketides with application in agriculture, medicine, and animal health.

9 Claims, 2 Drawing Sheets

6,303,767 B1

NUCLEIC ACIDS ENCODING NARBONOLIDE POLYKETIDE SYNTHASE ENZYMES FROM *STREPTOMYCES NARBONENSIS*

CROSS-REFERENCE TO RELATED APPLICATIONS

This application is related by claim of priority to provisional U.S. patent application Ser. No. 60/107,093, filed Nov. 5, 1998, and is a continuation-in-part of Ser. No. 09/320,878 filed May 27, 1999 U.S. Pat. No. 6,117,659 issued Sep. 12, 2000, each of which is incorporated herein by reference.

FIELD OF THE INVENTION

The present invention relates to polyketides and the polyketide synthase ("PKS") enzymes that produce them. The invention also relates generally to genes encoding PKS enzymes and to recombinant host cells containing such genes and in which expression of such genes leads to the production of polyketides. Thus, the invention relates to the fields of chemistry, molecular biology, and agricultural, medical, and veterinary technology.

BACKGROUND OF THE INVENTION

Polyketides represent a large family of diverse compounds synthesized from 2-carbon units through a series of condensations and subsequent modifications. Avermectin, candicidin, epothilone, erythromycin, FK-506, FK-520, narbomycin, oleandomycin, picromycin, rapamycin, spincoyn, tetracycline, and tylosin are examples of such compounds. Polyketides occur in many types of organisms, including fungi and mycelial bacteria, in particular, the actinomycetes. Given the difficulty in producing polyketide compounds by traditional chemical methodology, and the typically low expression of polyketides in wild-type cells that produce them naturally, there has been considerable interest in finding improved or alternate means to produce polyketide compounds.

This interest has resulted in the cloning, analysis, and manipulation by recombinant DNA technology of genes that encode PKS enzymes. For example, the following publications relate generally to the cloning of all or parts of the genes coding for the expression of PKS enzymes or other enzymes that act on polyketides of significant commercial interest or potential.

Avermectin
  U.S. Pat. No. 5,252,474 to Merck.
  MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
  MacNeil et al., 1992, *Gene* 115: 119–125, Complex Organization of the *Streptomyces avermitilis* genes encoding the avermectin polyketide synthase.
Candicidin (FRO008)
  Hu et al., 1994, *Mol. Microbiol.* 14: 163–172.
Epothilone
  U.S. patent application Ser. No. 60/130,560, filed Apr. 22, 1999, and Ser. No. 60/122,620, filed Mar. 3, 1999.
Erythromycin
  PCT Pub. No. 93/13663 to Abbott.
  U.S. Pat. No. 5,824,513 to Abbott.
  Donadio et al., 1991, *Science* 252:675–9.
  Cortes et al., Nov. 8, 1990, *Nature* 348:176–8, An unusually large multifunctional polypeptide in the erythromycin producing polyketide synthase of *Saccharopolyspora erythraea*.
Glycosylation Enzymes
  PCT Pat. App. Pub. No. 97/23630 to Abbott.
FK-506
  Motamedi et al., 1998, The biosynthetic gene cluster for the macrolactone ring of the immunosuppressant FK506, *Eur. J. biochem.* 256: 528–534.
  Motamedi et al., 1997, Structural organization of a multifunctional polyketide synthase involved in the biosynthesis of the macrolide immunosuppressant FK506, *Eur. J. Biochem.* 244: 74–80.
Methyltransferase
  U.S. Pat. No. 5,264,355, issued Nov. 23, 1993, Methylating enzyme from Streptomyces MA6858. 31-O-desmethyl-FK506 methyltransferase.
  Motamedi et al., 1996, Characterization of methyltransferase and hydroxylase 40 genes involved in the biosynthesis of the immunosuppressants FK506 and FK520, *J. Bacteriol.* 178: 5243–5248.
FK-520
  U.S. patent application Ser. No. 60/139,650, filed Jun. 17, 1999, and Ser. No. 60/123,810, filed Mar. 11, 1999. See also Nielsen et al., 1991, *Biochem.* 30:5789–96 (enzymology of pipecolate incorporation).
Lovastatin
  U.S. Pat. No. 5,744,350 to Merck.
Nemadectin
  MacNeil et al., 1993, supra.
Niddamycin
  Kakavas et al., 1997, Identification and characterization of the niddamycin polyketide synthase genes from *Streptomyces caelestis*, *J. Bacteriol.* 179: 7515–7522.
Oleandomycin
  Swan et al., 1994, Characterisation of a *Streptomyces antibioticus* gene encoding a type I polyketide synthase which has an unusual coding sequence, *Mol. Gen. Genet.* 242: 358–362.
  U.S. patent application Ser. No. 60/120,254, filed Feb. 16, 1999.
  Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.
Platenolide
  EP Pat. App. Pub. No. 791,656 to Lilly.
Rapamycin
  Schwecke et al., August 1995, The biosynthetic gene cluster for the polyketide rapamycin, *Proc. Natl. Acad. Sci. USA* 92:7839–7843.
  Aparicio et al., 1996, Organization of the biosynthetic gene cluster for rapamycin in *Streptomyces hygroscopicus*: analysis of the enzymatic domains in the modular polyketide synthase, *Gene* 169: 9–16.
Rifamycin
  August et al., Feb. 13, 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.
Soraphen
  U.S. Pat. No. 5,716,849 to Novartis.
  Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.
Spiramycin
  U.S. Pat. No. 5,098,837 to Lilly.

Activator Gene

U.S. Pat. No. 5,514,544 to Lilly.

Tylosin

EP Pub. No. 791,655 to Lilly.

Kuhstoss et al., 1996, *Gene* 183:231–6., Production of a novel polyketide through the construction of a hybrid polyketide synthase.

U.S. Pat. No. 5,876,991 to Lilly.

Tailoring enzymes

Merson-Davies and Cundliffe, 1994, *Mol. Microbiol.* 13: 349–355. Analysis of five tylosin biosynthetic genes from the tylBA region of the *Streptomyces fradiae* genome.

Each of the above-referenced patent applications, patents, and publications is incorporated by reference herein.

The cloning of PKS genes has been accompanied by advances in technology allowing one to manipulate a known PKS gene(s) either to produce the polyketide synthesized by the corresponding PKS at higher levels than occur in nature or in hosts that otherwise do not produce the polyketide. The technology also allows one to produce molecules that are structurally related to, but distinct from, the polyketide produced from a known PKS. See, e.g., PCT publication Nos. WO 95/08548; WO 96/40968; 97/02358; and 98/27203; U.S. Pat. Nos. 5,672,491; and 5,712,146; and Fu et al., 1994, *Biochemistry* 33: 9321–9326; McDaniel et al., 1993, *Science* 262: 1546–1550; and Cane et al., Oct. 2, 1998, Harnessing the Biosynthetic Code: Combinations, Permutations, and Mutations, *Science* 282: 63–68, each of which is incorporated herein by reference.

PKS enyzmes are similar to, but distinct from, the synthases that catalyze condensation of 2-carbon units in the biosynthesis of fatty acids. Two major types of PKS enzymes are found in nature: these types are commonly referred to as Type I or "modular" and Type II "aromatic" PKS enzymes. A third type sometimes referred to in the scientific literature is a "fungal PKS"; however, for purposes of the present invention, this type is to be considered a Type I PKS. These types differ in their composition and mode of synthesis of the polyketide synthesized. Type I PKSs are typically found in nature as complexes of multiple very large proteins. In this type, a set of separate catalytic active sites (each active site is termed a "domain", and a set thereof is termed a "module") exists for each cycle of carbon chain elongation and modification in the polyketide synthesis pathway.

The active sites and modules of a typical Type I PKS enzyme are shown in FIG. 9 of PCT patent publication No. WO 95/08548, which depicts a model of 6-deoxyerythronolide B synthase ("DEBS"), which is involved in the synthesis of erythromycin. Six separate modules, each catalyzing a round of condensation and modification of a 2-carbon unit, are present in DEBS. The number and type of catalytic domains that are present in each module varies, and the total of 6 extender modules and a loading module is provided on 3 separate proteins (designated DEBS-1, DEBS-2, and DEBS-3, with 2 modules per protein). The catalytic domains of the DEBS polypeptides provide a representative example of Type I PKS structure. In this particular case, the loading module and extender modules 1 and 2 reside on DEBS-1, extender modules 3 and 4 on DEBS-2, and extender modules 5 and 6 on DEBS-3; module 1 is the first module to act on the growing polyketide backbone, and module 6 the last. Each module of consists of at least two (if a loading module) and more typically three or more enzymatic activities or "domains."

A typical (non-starter) minimal Type I PKS module is typified by module 3 of DEBS, which contains a ketosynthase ("KS") domain, an acyltransferase ("AT") domain, and an acyl carrier protein ("ACP") domain. These three enzyme activities are sufficient to activate the 2-carbon extender unit and attach it to the growing polyketide molecule. Additional domains that may be included in a module relate to reactions other than the actual condensation, and include a ketoreductase activity ("KR") activity, a dehydratase activity ("DH"), and an enoylreductase activity ("ER"). With respect to DEBS-1, the first module thereof also contains repeats of the AT and ACP activities because it catalyzes initial condensation, i.e., it begins with a "loading domain" consisting of an AT and an ACP domain that determines the nature of the starter unit.

The "finishing" of the 6-deoxyerythronolide molecule is regulated by a thioesterase ("TE") activity in module 6. The TE activity catalyzes cyclization of the macrolide ring by formation of an ester linkage. In FK-506, FK-520, rapamycin, and similar polyketides, the ester linkage formed by the TE activity is replaced by a linkage formed by incorporation of a picolate acid residue. The enzymatic activity that catalyzes this incorporation for the rapamycin enzyme is known as rapP.

In PKS polypeptides, the regions that confer enzymatic activity (domains) are separated by linker or "scaffold"-encoding regions. These scaffold regions encode amino acid sequences that space the enzymatic activities (domains) at the appropriate distances and in the correct order. Thus, the linker regions of a PKS protein collectively can be considered to encode a scaffold into which the various domains (and thus modules) are placed in a particular order and spatial arrangement Generally, this organization permits PKS domains of different or identical substrate specificities to be substituted (usually at the DNA level) between PKS enzymes by various available methodologies. Thus, there is considerable flexibility in the design of new PKS enzymes with the result that known polyketides can be produced more effectively, and novel polyketides useful as pharmaceuticals or for other purposes can be made.

Type I PKS enzymes are encoded by "PKS gene clusters." PKS gene clusters usually consist of three or more open reading frames ("ORFs"), each encoding two or more modules of ketosynthase activity. For example, each of the DEBS polypeptides is encoded by a separate open reading frame (ORF). See Caffrey et al., 1992, *FEBS Letters* 304: 205, incorporated herein by reference.

As noted above in connection with reference to enzymes that cyclize linear polyketides, additional structural complexity in polyketides arises from or can be introduced by various activities, including glycosylation, hydroxylation, methylation, and other enzymatic activities. The rapP enzymatic activity mentioned above is an example of one such activity; another example is the hydroxylation of a polyketide by an oxidase enzyme similar in structure and function to the cytochrome P450 oxidase enzyme. The genes encoding such enzymatic activities are often found in relatively close proximity to the PKS genes and so may be considered part of a PKS gene cluster. By appropriate application of recombinant DNA technology, a wide variety of polyketides can be prepared in a variety of different host cells provided one has access to nucleic acid compounds that encode PKS proteins and polyketide modification enzymes.

The present invention helps meet the need for such nucleic acid compounds, recombinant PKS enzymes, and recombinant enzymes that modify polyketides by providing recombinant vectors that encode the narbonolide PKS enzyme and various narbomycin modification enzymes.

SUMMARY OF THE INVENTION

The present invention provides recombinant DNA vectors that encode the narbonolide PKS enzyme and various narbomycin modification enzymes. Illustrative vectors of the invention include cosmids pKOSO37-23, pKOSO37-24, pKOSO37-25, and pKOSO37-26.

The present invention also provides nucleic acid compounds that encode the various domains of the various modules of the narbonolide PKS from the narbomycin producing strain *Streptomyces narbonensis*. These domains include the KS, AT, ACP, KR, DH, ER, and TE domains. These compounds can be readily used, alone or in combination with nucleic acids encoding other PKS domains, as intermediates in the construction of recombinant vectors that encode PKS enzymes that make novel polyketides.

In one embodiment, the invention provides an isolated nucleic acid that encodes an activity of a polyketide synthase enzyme that synthesizes narbonolide, which is the key substrate for the synthesis of narbomycin. The encoded activity can be, for example and without limitation, a ketosynthase activity, an acyltransferase activity, or an acyl carrier protein activity. In another aspect, the invention provides an isolated nucleic acid that encodes a module, said module comprising a ketosynthase activity, an acyl transferase activity, and an acyl carrier protein activity. In another aspect, the invention provides an isolated nucleic acid that encodes an open reading frame, said open reading frame encoding two or more modules, at least one of which is derived from the narbonolide PKS. In another aspect, the invention provides an isolated nucleic acid that encodes a gene cluster, said gene cluster comprising two or more open reading frames. In another aspect, these isolated nucleic acids are incorporated within a recombinant expression vector.

In another embodiment, the invention provides an isolated nucleic acid that encodes a module in which at least one of the activities in the module is an activity of a non-narbomycin polyketide synthase. In one aspect, the invention provides an isolated nucleic acid that encodes an open reading frame comprising two or more modules, in which at least one of said modules is a module comprising an activity of a non-narbomycin polyketide synthase. In one aspect, the non-narbomycin polyketide synthase is either an erythromycin, a rapamycin, or a tylosin polyketide synthasee. In another aspect, these isolated nucleic acids are incorporated within a recombinant expression vector.

In another embodiment, the invention provides a method of preparing a polyketide, said method comprising transforming a host cell with a recombinant DNA vector that encodes a module of a polyketide synthase, said module comprising at least one narbomycin polyketide synthase activity, and culturing said host cell under conditions such that said polyketide synthase is produced and catalyzes synthesis of said polyketide. In one aspect, the method is practiced with a Streptomyces host cell. In another aspect, the polyketide produced is narbonolide or narbomycin. In another aspect, the polyketide produced is a polyketide related in structure to narbonolide or narbomycin. In another aspect, the polyketide produced is a polyketide related in structure to erythromycin, rapamycin, or tylosin.

These and other embodiments and aspects of the invention will be more fully understood after consideration of the attached Drawings and their brief description below, together with the detailed description, example, and claims that follow.

DETAILED DESCRIPTION OF THE INVENTION

Given the valuable pharmaceutical properties of polyketides, there is a need for methods and reagents for producing large quantities of polyketides, for producing polyketides in host cells that do not produce polyketides naturally, and for producing novel polyketides compounds not found in nature. The present invention provides such methods and reagents, with particular application to methods and reagents for producing the polyketide known as narbonolide and its derivative narbomycin (collectively referred to herein as "narbomycin") and novel compounds related through structure or genetics to narbomycin or the polyketide synthase that produces narbomycin.

In addition to providing methods for making narbomycin, the invention provides methods for making novel narbomycin analogs and derivatives, as well as reagents for making recombinant vectors that allow the production of narbomycin and its analogs in recombinant host cells of any origin. To obtain these reagents, genomic DNA was isolated from a narbomycin producing strain of *Streptomyces narbonensis*, partially digested with restriction enzyme SauIIIA1, and cloned into commercially available SuperCos™ cosmid vector (Stratagene) digested with restriction enzyme BamHI to produce a genomic library.

This library was then probed with a labeled probe specific for PKS gene sequences. This probing identified about several different cosmids. Cosmid DNA was isolated and analyzed by restriction enzyme digestion, which revealed that the entire PKS gene cluster was contained in overlapping segments on two of the cosmids identified. DNA sequence analysis using the T3 and T7 primers showed that the desired DNA had been isolated.

Further analysis of these cosmids and subclones prepared from the cosmids facilitated the identification of the location of various narbonolide PKS ORFs, modules in those ORFs, and coding sequences for narbomycin modification enzymes. The location of these genes and modules is shown on FIG. 1.

Figure 1:
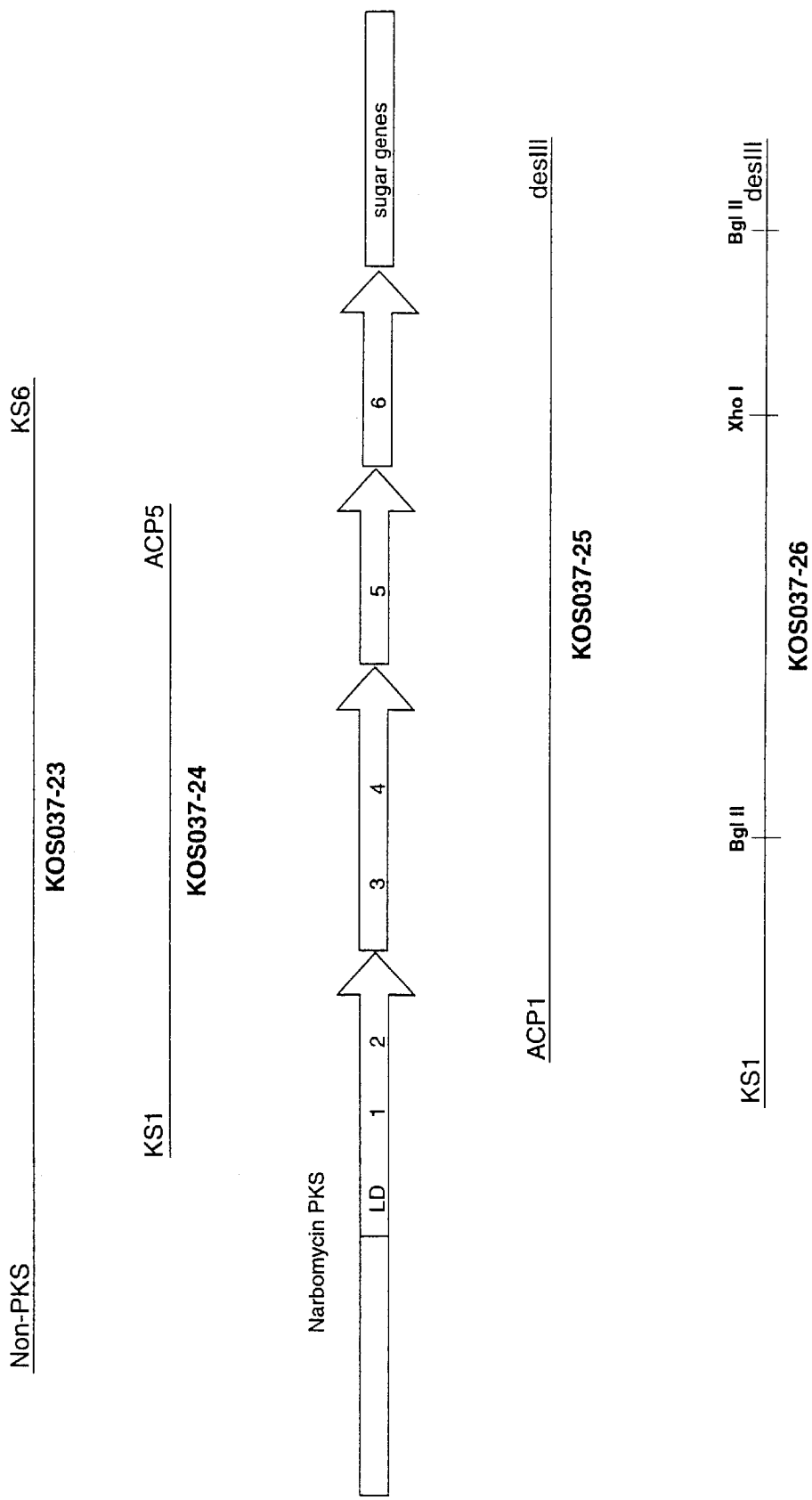
FIG. 1 shows a function maps of the insert DNA in various cosmids of the invention. The different cosmid inserts are identified with a reference number assigned to each cosmid, i.e., cosmid pKOSO37-23, pKOSO37-24, pKOSO37-25, and cosmid pKOSO37-26. The location of the coding sequences for modules 1–6 of the narbonolide PKS are also labeled (LD is the starter or loading module; 1 is extender module 1) as is the desosamine biosynthetic and transferase genes (labelled as "sugar genes").

FIG. 1 shows that the complete narbonolide PKS gene cluster is contained within the insert DNA of cosmids pKOSO37-23 and pKOS037-26 (insert size of ~44 kb). Each of these cosmids has been deposited with the American Type Culture Collection, Manassas, Va. 20110-2209, USA, in accordance with the terms of the Budapest Treaty (cosmid pKOS037-23 was deposited on Feb. 15, 2001 under accession no. ATCC PTA-3058; cosmid pKOS037-26 was deposited on Feb. 15, 2001 under accession no. ATCC PTA-3059). Various additional reagents of the invention can therefore be isolated from these cosmids. DNA sequence analysis was also performed on the various subclones of the invention, as described in Example 1 and in the sequence listing attached hereto. Based on the disclosure of this nucleotide sequence information as well as the known genetic code, the present invention provides a wide variety of useful compounds for constructing recombinant narbonolide PKS gene clusters, ORFs, modules, domains within modules, and modification enzymes.

Thus, the invention provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form. These DNA molecules comprise one or more sequences that encode one or more domains (or fragments of such domains) of one or more modules in one or more of the ORFs of the narbonolide PKS gene cluster. Examples of such domains include the KS, AT, DH, KR, EH, ACP, and TE domains of at least one of the loading and 6 extender modules of the four ORFs of the narbomycin gene cluster.

In one preferred embodiment, the invention provides a recombinant DNA vector that encodes the narbonolide PKS in three, as opposed to the naturally occurring four, ORFs. The recombinant vector codes for expression of a polypeptide that results from fusing the separate ORFs for modules 5 and 6 of the narbonolide PKS into a single ORF. The recombinant vector can be used to produce either narbomycin or picromycin (depending on choice of host cells and the presence of polyketide modifying enzymes) in recombinant host cells with decreased production of the 12-membered macrolactones as compared to the naturally occurring host cells that produce narbomycin and picromycin.

As the preceding discussion illustrates, in an especially preferred embodiment, the DNA molecules of the invention are recombinant DNA expression vectors or plasmids. Such vectors can either replicate in the cytoplasm of the host cell or integrate into the chromosomal DNA of the host cell. In either case, the vector can be a stable vector (i.e., the vector remains present over many cell divisions, even if only with selective pressure) or a transient vector (i.e., the vector is gradually lost by host cells with increasing numbers of cell divisions).

Thus, the various PKS-encoding nucleic acids of the invention can be cloned into one or more recombinant vectors individually or in combination with other nucleic acids. Each activity-encoding nucleic acid can be inserted into the vector with its own separate control elements, or multiple activity-encoding segments can be under the control of a single promoter in the vector. The PKS component nucleic acids of the invention therefore often include flanking restriction sites to allow for facile deletion, insertion, or other manipulation to assist in the construction of expression vectors. The implementation of restriction sites to facilitate vector construction is known to those of skill in the art and can be accomplished using the commonly known techniques, including those described below, such as site-directed mutagenesis and PCR.

The recombinant vectors of the invention will typically include suitable control sequences, or promoters, which include those which function in eucaryotic or procaryotic host cells. Preferred hosts cells for purposes of promoter selection for practice of the present invention include fungal cells, such as procaryotic cells, including Streptomyces cells, and eukaryotic cells, such as yeast and mammalian cells. Suitable control sequences for such cells are well known in the art. Control systems for expression in yeast, including control systems that include not only promoters but also enhancers, translation control sequences, such as ribosome-binding sites, and optionally sequences that direct of secretion are widely available and routinely used.

Particularly useful promoters for procaryotic host cells include those from PKS gene clusters that result in the production of polyketides as secondary metabolites, including those from aromatic (Type II) PKS gene clusters. Examples are act promoters, tcm promoters, erythromycin promoters, spiramycin promoters, promoters from antibiotic resistance-conferring genes including but not limited to ermE, and the like. However, other bacterial promoters, such as those derived from sugar metabolizing enzymes, such as galactose, lactose (lac) and maltose, are also useful. Additional examples include promoters derived from genes that encode biosynthetic enzymes such as for tryptophan (trp) or beta-lactamase (bla), and bacteriophage promoters, such as the lambda PL and T5 promoters. In addition, synthetic promoters, such as the tac promoter (U.S. Pat. No. 4,551,433), can be used.

Particularly useful promoters and control systems are those that activate transcription of ORFs and accordingly translation of the mRNA and expression of protein during transition of the host cell from growth to stationary phase (as occurs, for Streptomyces, in the vegetative mycelium). The control system contained in the plasmid identified as pCK7, i.e., the actI/actIII promoter pair and the actII-ORF4 gene (an activator gene), is particularly preferred. See U.S. Pat. Nos. 5,672,491 and 5,712,146, each of which is incorporated herein by reference. Generally, it may sometimes be desirable to allow for regulation of expression of the PKS gene cluster relative to the stage of growth of the host cell. Illustrative regulatory control sequences are known to those of skill in the art; examples include promoters that cause the expression of a gene to be turned on or off in response to a chemical or physical stimulus, including the presence of a specific compound.

Selectable markers can also be included in the recombinant expression vectors of the invention. A variety of selectable markers are known which are useful in selecting for transformed cell lines and generally comprise a gene whose expression confers a selectable phenotype on transformed cells when the cells are grown in an appropriate selective medium. Such markers include, for example, genes which confer antibiotic resistance, i.e., the tsr gene, which confers resistance to the antibiotic thiostrepton and is commonly used to select recombinant Streptomyces cells, or sensitivity to the plasmid. Alternatively, several polyketides are naturally colored, and this characteristic provides an alternative marker for screening cells successfully transformed with certain vectors of the invention.

Methods for introducing the recombinant vectors of the present invention into suitable hosts are known to those of skill in the art and typically include the use of $CaCl_2$ or other agents, such as divalent cations, lipofection, DMSO, protoplast transformation and electroporation. For Streptomyces cells, viral infection and conjugation are commonly used methods for transformation.

Particularly preferred host cells for certain applications of the present invention are those that do not otherwise (i.e., in the absence of transformation with a vector of the invention) produce a polyketide. Choice of such a host cell makes easier the determination that transformation has occurred as well as purification of the polyketide produced. Illustrative host cells of this type include the modified *Streptomyces coelicolor* CH999 host cell and other host cells described in U.S. Pat. Nos. 5,712,416 and 5,672,491, each of which is incorporated herein by reference. See also, U.S. patent application Ser. No. 60/101,557, filed Sep. 22, 1998, and the related application by claim of priority filed Oct. 28, 1998, Ser. No. 09/181,833, by the same inventors, both of which are incorporated herein by reference. Other host cells that can be utilized for purposes of the present invention include *E. coli*, mammalian, Myxobacteria, Saccharomyces, Saccharopolyspora, Streptomyces, yeast, and plant cells; see, e.g., PCT patent publication No. WO 98/27203 and U.S. patent application Ser. No. 09/114,083, filed Jul. 10, 1998, both of which are incorporated herein by reference.

The recombinant DNA vectors and host cells of the invention can be used not only to produce narbomycin but also to produce other polyketide and polyketide-related compounds. In one aspect, the invention provides nucleic acids that encode a mutated form of a naturally-occurring narbonolide PKS domain, module, ORF, and gene cluster, and so can be used to prepare a narbomycin-related compound.

In one preferred embodiment, the starter domain of the narbonolide PKS is inactivated, i.e., by deletion, addition, or substitution of one or more codons in the recombinant DNA that encodes the PKS. In one preferred aspect, the starter domain is inactivated by site-specific mutagenesis to inactivate the active site. The resulting PKS can be used in host cells (optionally lacking an endogenous PKS) that are fed non-naturally occurring diketides to make non-naturally occurring oleandolides and narbomycin-like compounds. This technique is more generally described elsewhere. See U.S. Pat. No. 6,066,721, issued on May 23, 2000, and PCT patent publication No. 97/02358, each of which is incorporated herein by reference.

Mutations can be introduced to the nucleic acid compounds of the invention using conventional techniques. The substrates for mutation can be an entire PKS gene cluster, or can be nucleic acids that encode an ORF, a module, or a domain. Techniques for introducing mutations include preparing synthetic oligonucleotides including the mutations and inserting the mutated sequence into the appropriate vector using restriction endonuclease digestion. See, e.g., Kunkel, 1985, *Proc. Natl. Acad. Sci. USA* 82:448; Geisselsoder et al., 1987, *BioTechniques* 5:786.

Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by regulating primer length and base composition and by keeping the mutant base centrally located. See Zoller and Smith, 1983, *Methods in Enzymology* 100:468. Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations. See, e.g., Dalbie-McFarland et al., 1982, *Proc. Natl. Acad. Sci. USA* 79:6409. One can also use PCR mutagenesis to effect the desired mutations. See U.S. Pat. No. 5,605,793.

Random mutagenesis of selected portions of nucleic acids encoding enzymatic activities can be accomplished by several different techniques. These techniques include inserting an oligonucleotide linker randomly into a plasmid, irradiating with X-rays or ultraviolet light, incorporating nucleotides during in vitro DNA synthesis, performing error-prone PCR mutagenesis, preparing synthetic mutants, and treating plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In another embodiment, the invention provides polyketides other than narbomycin by providing expression vectors that encode a chimeric PKS. The chimeric PKSs of the invention can be conceptually viewed as those substantially patterned on either the narbonolide PKS or a non-narbonolide PKS. In either case, the chimera includes one or more functional domains of the narbonolide PKS or a mutated version of such a domain. The invention also provides recombinant DNA vectors and host cells containing those vectors in which the chimeric PKS is produced together with one or more polyketide modification enzymes. Such enzymes can include, for example, a TE or its picolate-acid incorporating homologue, a rapP homologue, a methyltransferase, one or more sugar biosynthetic enzymes or transferases, a hydroxylase, or a P450 oxidase homologue.

With respect to chimeric PKS gene clusters, ORFs, and modules, preferred examples include construction of chimeric PKS enzymes wherein the erythromycin, FK-506, FK-520, narbomycin, oleandomycin, picromycin, rapamycin, spirarnycin, or tylosin PKS gene clusters function as accepting scaffolds or ORF, module, or domain donors. In this regard, the examples of erythromcyin PKS, rapamycin PKS, and tylosin PKS are preferred for constructing chimeric PKS gene clusters for production of polyketides with antibiotic activity.

Those of skill in the art will recognize that it is not necessary to replace an entire domain, module, or ORF of the target (scaffold) PKS with a corresponding segment of the narbonolide PKS. Rather peptide subsequences of a narbonolide PKS domain segment that correspond to a peptide subsequence in the scaffold PKS, or which otherwise provide useful function, can be used. In this context, the term "scaffold" defines the target PKS encoding DNA having one or more domain fragments, domains, modules, or ORFs that are being replaced, for example by a corresponding narbonolide PKS gene cluster segment.

Accordingly, appropriate nucleic acids, typically DNA, for construction of such chimeric PKS include those that encode at least 10, 15, 20, or more amino acids of a selected narbonolide PKS segment or domain. See, e.g., provisional U.S. patent application Ser. No. 60/091,526, filed Jul. 2, 1998, incorporated herein by reference. Of course, portions of, or all of, the desired coding sequences can be synthesized using standard solid phase synthesis methods, such as those described by Jaye et al., 1984, *J. Biol. Chem.* 259:6331, and which are available commercially from, for example, Applied Biosystems, Inc.

Thus, the invention provides recombinant materials for the production of PKS genes or gene clusters, as well as "combinatorial" libraries of PKS expression vectors and the corresponding polyketides, wherein the term "combinatorial" reflects that the library encompasses a variety of different PKS gene clusters and corresponding polyketides. Of course, the methods of the invention may also be directed to the preparation of a single polyketide. The resulting polyketides may be further modified to convert them to compounds useful for a particular purpose, such as an antibiotic or an antifungal, for example.

Thus, in another aspect, the invention is directed to a multiplicity, or a library, of cells comprising PKS genes, wherein each different cell of the library contains an expression vector for the production of a different modular PKS. In a preferred embodiment, the different PKS are derived from the narbonolide PKS. In another preferred embodiment, the library of different modular PKS is obtained by modifying one or more domains or modules of a PKS ORF or gene cluster. The invention also provides methods to produce libraries of PKS complexes and libraries of polyketides by culturing these cells or by the use of cell-free extracts. See PCT patent publication No. 97/02358, incorporated herein by reference.

Each individual and unique colony in a library of the invention has the ability to produce a particular PKS synthase and ultimately a particular polyketide. Typically, there will be duplications in the colonies; the subset of the transformed colonies that contains a different PKS in each member colony can be considered the library. Alternatively, the expression vectors can be used individually to transform hosts, which transformed hosts are then assembled into a library. The number of different polyketides that are produced by the library is typically at least four, more typically at least ten, preferably at least 20, more preferably at least 50 or more, reflecting similar numbers of different altered PKS gene clusters and PKS gene products. The number of members in a library of the invention can be determined by the applications of the practitioner. The degrees of freedom are large, i.e., the variation of starter and extender units, stereochemistry, oxidation state, and chain length are attributes that can be varied. Thus, the present invention allows the construction of very large libraries based on the narbonolide PKS.

Colonies in the libraries of the invention produce the relevant PKS enzymes and can produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand or exposure to a cell. Binding can be detected either directly or through a competition assay. Means to screen such libraries for binding are well known in the art. Alternatively, individual polyketide members of the library can be tested against a desired target. In this event, screens wherein the biological response of the target is measured are preferred.

Those of skill in the art will recognize that, in providing libraries of PKS gene clusters, the invention also provides each individual PKS gene cluster in the library. In one embodiment, these members each comprise a polyketide synthase gene cluster derived from a naturally occurring PKS. In another embodiment, each member contains at least two functional PKS modules, and one or both of these modules contains mutations, deletions, or replacements of one or more of the activities of the naturally occurring module. In another embodiment, each member produces a polyketide not found in nature.

Particularly preferred embodiments of the invention include those recombinant PKS enzymes and PKS modules, ORFs, and gene clusters in which a KS, AT, ACP, KR, DH or ER has been either deleted or deleted and replaced. If replaced, the activity or domain can be replaced by a version of the activity from a different PKS or from another module within the same PKS gene cluster. Also preferred are derivatives where at least one non-condensation cycle enzymatic activity (KR, DH or ER) has been deleted or wherein any of these activities has been mutated so as to change the polyketide produced from the PKS. In another embodiment, the domain or module of one PKS, such as from erythromycin, rapamycin, or tylosin is replaced with that of a narbonolide PKS domain or module. Such methods are applicable also to fragments of domains, such as those encoding an active site.

In constructing a recombinant chimeric PKS module, ORF, or gene cluster of the invention, a variety of embodiments are provided. In one embodiment, one can select the polyketide chain length by selecting the appropriate number of modules in the PKS gene cluster. In another, one can determine the nature of the carbon skeleton of the polyketide by selecting the specificities of the acyl transferases that determine the nature of the extender units at each position— e.g., malonyl, methyl malonyl, ethyl malonyl, and the like. In another, one can select the appropriate loading domain specificity to effect the desired carbon skeleton of the polyketide. In another, one can select the oxidation state at various positions of the polyketide by selecting the appropriate, if any, dehydratase and reductase domains of the modules to determine the presence and location of ketone, alcohol, alkene or alkane substituents at particular locations in the polyketide. In yet another embodiment, one can select the stereochemistry of the resulting polyketide by selecting the AT/KS specificity (as when there is no reductive cycle or the reductive cycles consists of only a ketoreductase); by selecting the ketoreductase to determine the chirality of any alcohol; and by selecting the enoyl reductase specificity.

Thus, the invention provides methods for constructing PKS modules, ORFs, and gene clusters by deleting or inactivating domains or modules, inserting domains or modules the same or different PKS systems, or by otherwise mutating such compounds using standard procedures for obtaining genetic alterations. Thus, to obtain nucleic acids encoding a variety of derivatives of a PKS gene cluster, and thus a variety of polyketides, as in the construction of a library, a desired number of constructs can be obtained by "mixing and matching" PKS domains, modules, and ORFs. If replacement of a particular target region in a host PKS gene cluster, ORF, or module is to be made, this replacement can be conducted in vitro using suitable restriction enzymes. This replacement can be effected in vivo using recombinant techniques involving homologous segments of nucleic acid framing the replacement gene in a donor plasmid and a receptor region in a recipient plasmid. Such systems, advantageously involving plasmids of differing temperature sensitivities, are described, for example, in U.S. Pat. Nos. 5,712,416 and 5,672,491, incorporated herein by reference.

Thus, the invention provides useful reagents and methods for the production of polyketides. In one aspect, the invention provides recombinant vectors encoding the complete PKS gene cluster and associated modification enzymes for the polyketide narbomycin. In another embodiment, the KS domain of the PKS is inactivated, preferably by site-specific mutagenesis of the corresponding coding sequence, and non-natural activated diketides are fed a strain harboring the mutant PKS (in the chromosome or in an extrachromasomally replicating vector) to produced a desired compound.

This technique is more fully described in PCT patent application No. US98/14911 and U.S. Pat. No. 6,066,721, issued on May 23, 2000, both of which are incorporated herein by reference.

In another aspect, the invention provides nucleic acids that encode the various domains, including the KS, AT, ACP, KR, DH, ER, and TE domains of the loading and all six extender modules of the narbomycin gene cluster. In another aspect, the invention provides nucleic acids that encode the modification enzymes that encode the activities that modify the narbomycin polyketide. In particular, the present invention provides in recombinant form the desosamine biosynthetic and transferase enzyme. In another aspect, the invention provides mutated versions of the foregoing that differ from their unmutated counterparts in activity or specificity. In another aspect, the invention provides chimeric PKS modules, ORFs, and gene clusters comprising one or more domains of the narbonolide PKS (or a mutant form thereof) and one or more domains of a non-narbonolide PKS. Further, the invention provides host cells comprising such vectors, methods of culturing host cells to produce the recombinant PKS of the invention as well as the polyketides produced by those PKS, and a variety of novel polyketides.

EXAMPLE 1

Narbonolide PKS Sequence

To facilitate the construction of the nucleic acids of the invention, cosmids pKOSO37-23, pKOSO37-25, and pKOSO37-26 of the invention have been subjected to DNA sequence analysis. The SuperCos™ vectors (Stratagene) from which these cosmids were derived comprise sequencing sites called T3 and T7 that facilitate sequencing.

Figure 2:
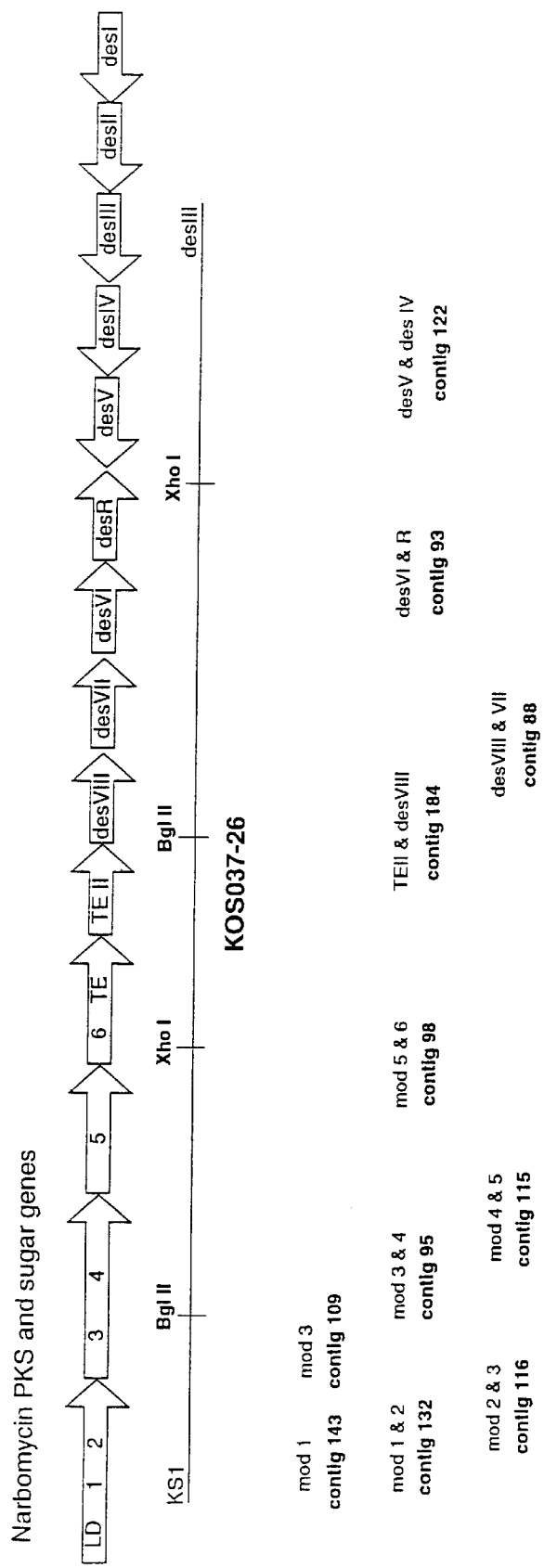
FIG. 2 shows a restriction site and function map of cosmid pKOS037-26. Various restriction sites (BglII, EcoRI) are also shown. The ORFs and modules of the narbonolide PKS and narbomycin modification enzymes are also shown, together with contigs identifying the contig sequences shown below.

Each sequence is preceded by a contig number. This number is also shown on FIG. 2 below the region of the insert DNA in cosmid pKOSO37-26 from which the sequence is obtained. Contig 143 is composed of two sequences, designated 143a and 143b, below.

Contig 143a (SEQ ID NO:1)
ACAGGGGATATCCCGCTCCAGGCGAACG-GTAGCCGCGTGCCCTCGCCGAACGC-CCCGCCCGCACC GGCCGCCTGCACGGCGGCGTC-GAGCAGCGCCGGGTGGAGGCCGAACCGCGCGCCC TCGGCGCCCG CGACCTCCGTCGGCAGGGC-CACGTCGGCGAACACCTCTTCGCCGCGC-CGCCAGACGCCACGGACG CCCCGGAAGAGGGGC-CCGTAGCCGTATCCGCTCGCCGCGAAGCGGTCGTAC AGACCGTCCACGTC CACTGCTTCGGCACCCGC-CGGGGGCCAGGCCTCCGGGTCGGCGA-CAGGGGCGGTGCGATCCGTAC GGGCGAGCACAC-CGGTCGCGTGCCGCGTCCACTCCGGCTCGCCCGGC GCGTCCTCCGGGTGCGCG TGGAGCACGAAGG-TACGGCGCCCGGACTCGTCGCTCGCGC-CGACGGACAGCTGCACGCGGACCGC GCCGC-GACGGGGCAGGACGAGCGGGGCGTCGAGGGTGAG CTCCTCGACCAGAT CGCAGCCGACCT GGTCACCGGCCCGGAAGGC-CAGCTCCACGAACGCCGTTCCCGGCAG-CAGCACCGTGCCGGCCACC GCGTGGTCCGCCAGC-CAGGGGTGCGTACGGAGGGAGAGGCTCCCCGTGA G CAGGCAGCCGTCGGA GTCGGCGAGCGCGACG-GCCGCGCCGAGCAGCGGGTGCTCGGC-CGCCCCGAGACCGGCGGACGTGA TGTCACCGACG-GCGGAGTGCTCGGGCCGCGGCCAGTAGCGCTCGGT CTGGAAGGCGTAGGTGGGG AGGTCGGGGAG-GTCGGCGTTCGTCGCGTTCTTCGTG-GTCGTGGTGGG-GAGGACGGGTGTCCAGTC GAGGGGGAGGCCGT-TGGTCCAGGCCTCGGCGAGCGAGGTGACCAGACGC TCCTGGCCGCCGTCCT CGCGGCGGAGGGTGC-CGAGGCCGGTGACGGTGTCGGGGAGGGC-CATGGTGAGGACGGGGTGGGCG CTGACCTCGAC-GAAGTGGGTGAACCCTTCGTCGGTGGCGAGGGTT CGACGGCGGGGGCGAAGCC GACGGGGTGGCG-GAGGTTGCGGTACCAGTACGTGGCGTC-GAGGGCGGGTTCGGTGATCCAGGCAC CGTC-GAGCGTGGAGAAGAAGGGGACGCGCGGAGCGTGC GGGGTGAGTCCG GCGAGGACGTCGGCG AGCTCGTTCTCGATGGTCTC-GACGTGGGCGCTGTGGGAGGCGTAGTC-GACGGGGATGATCCGCGC GCGGATGCCGTCGGC-CTTGCAGGTCTTCGCGAGCTCTTCGATCTGTGCGG GGTCGCCGGAGACCA CGGTGGCGGTGGGGCCGT-TGACGGCGGCGATCGACAGTCCGTC-GAGGGTGTCGATCCGCTCCAGG ACGTCGGCCTG-GCTGAGGGCGAGGGAGACCATGCCGCCCCTGCCGG CGAGGTGAGCGGCGATGGACCGGCTGCG-TAGGGCGACGACGCGGGCGGCATCCTC-CAGGCTCAGTGCCCCGGCGACGTACGCGG CGGC-GATCTCGCCCTGGGAGTGGCCGATGACGGCCTGGG GGGTGATG CCGTGGTGCTGCCAGATCTTCGC-GAGGGAGACCATGACGGCGAAGGTG Contig 143b (SEQ ID NO:2)
CGGGCTGGACGACGTCGACGCGGTC-GAGCGTCGGGGCGCCGGGAGCCTGTCG-TACGACGGCTTCG AGGGACCAGTCGACGTGACGG-GAGAGCGCGGTCTCGCACGCGGCCATCTCCGCCGC GAACTCCGC AGAGGAGTCCAGCAGTTCGGCAC-CCATCCCGGACCACTGCGTGCCCTGGC-CGGGGAACACGAACG CCACGCGCCCGACAGCG-GAAGCCGTGCCACGAATCAGCCCGTCCGGGTCGGC CAGGGCCTGTACG AGGTCGCCCGCCCCGGTGC-CCAGCGCGACGGCCCGGTGCTCGAACT-GCGCCCGCCCGTCGGCCAG TACGCGGGCGACG-GCGCCGGCGTCGACGTCATCCGTACGCCCCTGAGA GGCGTACGCGGCGAGCC GCTCGATCTGGGCGTC-GAGTGCACCGGCGGACTTCGCCGACAC-CACCCACGGCACCACGCCACCC GACGACG-GCTCGTCCACGGCGGTGTTTCCACCGTCGGGGCCT CTTCGAGGACGACGTGAGCGTT CGTCCCGCTGAT-GCCGAAGGAGGAGACGGCGGCGCGGCG-CAGCCCGCCGTCCTGCTTCTCCGGCC AGTCCACG-GCCTCGGTGAGGAGTTCCACGGCACCGGCCGACCA GTCGATCT GGTCCGAGGGGGCG TCCACGT-GAAGCGTCTTCGGGAGTAGCCCGTGGCG-CATCGCCTGGACCATCTTGATGACACCGGC GACACCGGCCGCGGCCTGGGTGTGC-CCGATGTTGGACTTCAACGATCCGAGCAGCA ACGGACGTT CGCCGCCCGGTCCTGCCCGTAG-GTGGCGATCAGGGCCTGCGCCTC-GATCGGGTCGCCGAGCCGC GTCCCGTGCCGT-GCGCCTCGACGACATCGACCTCGCCCGGCGTGAGC CGGGCGTCGGCCAGGGC CCGCCGGATGACGCGCT-GCTGCGACGGCCCGTTCGGAGCCGT-GAGACCGTTGCTGGCGCCGTCCT GGTTCACG-GCGCTGCCGCGGACGACCGCGAGGACCCGGTGTCC GTGGCGGCGGGCGTCCGACAGG CGCTCGACGAG-GAGGACACCGACAC- CCTCGGACCAACTGGTGCCGTCCGC-
CGACGCGGCGAACGC CTTCGACCGACCGTCCCCG-
GCCAGCCCGCGCTGCCGGCTGAACTCCACGAACAT
CCCGGCGTGG GCATCACGGCCACGCCGCCGGC-
GAGCGCCATGTCGACCTCGCCCTTGCG-
CAGGGCCTGCACGGCG AGGTGCAGGGCGAC-
CAGCGACGACGAGCAGGCGGTGTCCACCGTCAGGG
CGGGGCC
CTCAAGGCC GAGCGTGTACGAGACGCGGCCCGA-
CATCACGCTGGCCGTGTTGCCGGTCAG-
CAGGTATCCGTCGA GGCCCTCCCCGCCGTCGCG-
CAGGCTCGGCCCGTACTCGTGGGTCATCGCCCCGG
Contig 132 (SEQ ID NO:3)
GAACCCGTCGGCGTCCGCCGAGAAGGC-
CTTGCTCCGGCCGTCCGGGCGAGCGC-
CCGCTGCCGGC TGAACTCCACGAACATGT-
GCGGGGTCGCCATCATCGCCACACCACCGGCGAG
TGCCATCGAGCAT TCACCGCTCCGCAGCGCCCG-
CACCGCCAGGTGCAGGGCCGGTCAGCGAG-
GACGAGCAGGCGGTGTC GACGGTCGTCGCGGGC-
CCTTCGAGACCGAAGGTGTACGCGATGCGGCCGGA
CGCGACGCTCGGCG TGCTGCCGGTCAGCAGG-
TAACCCTCCACGCCGCGCGGGGCGT-
TCGGGACGCGGGCCGCGTAGTCC TGGTAGGAGAG-
GCCGATGAAGACACCGGTGCTGCTGCCGCGCAGCG
ACCCGGCTCGATGCCGGC CCGCTCGAACGCCTC-
CCAGGACGTCGCCAGGAGCATCCGCT-
GCTGCGGGTCCATGGCGAGCGCCT CGCGCGGC-
GAGACACCGAAGAACTCCGCGTCGAACTCGGCCGC
GTCGTGCAGGAACCCGCCCTCG CGGACGTACGC-
CTTGCCGAGCGCGTCCGGGTCGGCGTCG-
TACAGGCCGTCGAGGTCCCAGCCCCG GTCG-
GTGGGGAAGGGCGTGATGCCCTCGCCGCCCTCGGC
CAGCATCCGCCACAGGTCTCAGGGC TGCGGATGC-
CACCGGGGTATCGGCAGCTCATGGCGAC-
GATCGCGATCGGATCGTCGTCGACACCG AGAC-
CGACACCGAGACCGAGACCGACACCGAGACCGAC
ACCGGATCCGCCCCGACACCGGATCC GCCAC-
CGAGACCAGCACCAGCTCCGCCAC-
CGAGACCAGCACCAGCTCCGGCAC-
CGAGACCAGCGC
CGACAGCCCGCGTCCCCCTGGC-
CCACGTGGACTCCGCCGCCGCGTC-
CTCGTCACCGAGGAACTCGGCACGGAG-
CAGTGACGCGAGGGCCAGCGGCGTCGGGTGGTC
GAAGACGAGCGTCGCGGGCAAGGG GAGCCCG-
GTCGCCCGGGTCAGCCGGTTGCG-
GAGCTCGACTCCGGCGAGCGAGTC-
GAAGCCGATGT
CCTTGAAGGCCCGGTCGGCGGCGACGTC-
CTCAGGTGAACGCATCCGGAGCACGGCG-
GCGGCCTGG GCCCGTACGAGACCGAGGAG-
GATCTCCGTACGCTCGCCGGGAGCCGCGGCGGCCA
GCCGCTCGGC CAGCGGGTTCCCGCCCGCGGCG-
GAGCTGCCGCCCGGCCCGGC-
CGGGGCGCTCTCCCGCGCGTCGA TGATGCGCCG-
CACCTCGGGCAGCTCCTCGACGAGGGGCT
GAGGGCGGCCGGAGGAGTACGCGAGG
TAGAAACGGTCCCAGTCGATGTCCGC-
GACGGTGATCGCGGTCTCGTCCCGGC-
CGAGGGCGGACTC CAGTGCGGTCAGGGCGAGT-
TCCGGGTCCATGCCGGGTACGCCG
TGATCGCGCAGGCGCTCGGCCA CCCC
Contig 116 (SEQ ID NO:4)
AGCGGGCCAGGCCGGAGCCGGGGACCGG-
GACCGGGACGTGTCCACGCCGTCCAG-
GAGCACCGCCC ACACGGATGCCCTGCTGGCA-
CAACTCACCAGGCTGGAAGGCGCCTTGGTGCTGA
CGGGCCTCCCG GGCGCCCCGGGAGCGAA-
GAAGTCCTGGAGCACCTGCGCTCCCT-
TCGCGCGATGGTCACGGGCGA GACCGGGAGCGG-
GACCGGGGCCGGAAGCGGGGGCGGGGGCGCGTCC
GCGGAATCCGGGGGCGGAG ACCCCTACTACGC-
CGACGGGGGCGGGAGTGAGGAC-
CGCGCGGGAGTGCCGGACTTCATGAACGCC TCG-
GCCGAGGAACTCTTCGGCCTCCTCGACATGGACCCC
AGCACGGACTGATCCCTGCCGCACGG CCGCCTC-
CCGCCCCGGGCCCCGTCCGAGAC-
CCCGTCCCGGACCCGTCCCGGGCACCTCGACTCGA
ATCACTTCATGCGCGCCTCGGGCGCCTC-
CAGGAACTCAAGGGGACAGCGT
GTCCACGGTAACGA AGAGAAGTACCTCGACTAC-
CTGCGTCGCGCCACGGCGGACCTCCAC-
GAGGCCCGCGGCCGCCTCC GCGAGCTGGAGGC-
CAGGGCGGGCGAGCCGGTGGCGATCGTCGGCATGG
CCTGCCGCCTGCCGGGC GGTGTCGCCTCGCCG-
GAGGACCTGTGGCGGCTTGTGGCCGGTG-
GCGAGGACGCGATCTCGGAGTT CCCGCAGGAC-
CGCGGCTGGGACGTGGAGGGGCTGTACGACCCGAA
CCCGGAGG
CCACGGGCAGGA GTTACGCCCGTGAGGCCGGAT-
TCCTGTACGAGGCGGGCGAGTTCGACGC-
CGACTTCTTCGGGATC TCGCCGCGCGAGGC-
CCTCGCCATGGACCCGCAGCAGCGGCTCCTCCTGGA
GGCC
TCCTGGGAGGC GTTCGAGCACGCCGGCATCCCG-
GCGGCCAGTGCGCGCGGCACGTCGGTCG-
GCGTCTTCACCGGCG TGATGTACCACGACTACGC-
GACCCGTCTCACCGACGTCCCCGAGGGCATCGAG
GGCTACCTGGGC ACCGGGAACTCCG-
GCAGCGTCGCCTCGGGCCGGGTCGCCTA-
CACGCTGGGCCTGGAGGGCCCGGC CGTCACGGTC-
GACACGGCCTGCTCGTCCTCGCTCGTCGCCCTGCAC
CTCGCCGTG
CAGGCCCTGC GCAAGGGCGAGGTCGACATG-
GCGCTCGCCGGCGGCGTGACGGTCAT-
GTCGACTCCCAGCACCTTC GTCGAGTTCAGCCGC-
CAGCGCGGACTGGCCCCCGACGGCCGGTCGAAGTC
CTTCTC
GTCGACGGC GGACGGCACCAGCTGGTC-
CGAGGGCGTCGGCGTCCTCCTCGTC-
GAGCGCCTGTCGGACGCCCGTC GCAAGGGCCAC-
CGGGTGCTCGCCGTGGTCCGGGGCACGGCCGTCA
ACCAGGACGGCGCGAGCAGC GGCCTCACCGC-
CCCGAACGGCCCGTCTCAGCA
Contig 109 (SEQ ID NO:5)
GGTGCTCCAGGGCGGCGACCCTGCCCAT-
GCCCCACACCATGGCCTGGGCGGGGGAG-
GAGATGTGG TCGGCGCGGCCGACGGACAC-
CGCGCCACGGGTGACGCACCACAGCGGAGCGGC
GACACCGGCGTC CTCCAGCGCCTGCACCAGGGT-
GAGGGTGGCGCCGGTGCCCGGGT-
GAAGGGGCGGGGTGGCCGG GGTGCGCGTC-
CTCGTCCCAGGCGAGCAGCGAGACGACACCGCCG
ACGGCTCCACCGGCCGCCGCC AGGGCTTCGC-
CCAGCGCCTCCGTGAGCCGCGTGCCG-
GTCGCTCGGTGCGGACACGTCCAGCCGTAC
GGGGTCGGCGCCCGCACCGGACAGCGCG-
GCGAGCACCGGGGCGGCCTCGGAGG
ACCGGCCCTCGG GGGCGACGACGAGCCAGCGAC-
CGGACAGGCCGGGGCTCTCGGTGC-
CCTCGGCGACCGCGAGCCGC TTCCAGTCGACGCG-
GTAGCGCCAGGAGTCCTGCACGGAGCCCTGGGCGG
CGGGGGAGT CGTGGAG CCAGTAGTGACGGCGCTGGAAGGCG-
TAGGTGGGGAGGTCGGGGAGGTCGCCG-
GTCGCGGCCGGGA GGACGGGCGCCCAGTCGACG-
GTGAGGCCGTGGGCCCAGGCTTCGGCGAGGGAGG
TGATCAGGCGG TCGAGGCCGCCTTGTTCGCGGCG-
GAGGGTGCTGAGGCCTGTGACGGT-
GTCGGGGAGGGCCATGGT GAG-
GACGGGGTGGGCGGAGACCTCGATGAAGTGGGTG
AAGCCTTCGGTTGTGGCGAGGGTTTCGA
TGGCGGGGGCGAAGCCGACGGGGTGGCG-
GAGGTTGCGGTACCAGTAGGTGGCGTC-
GAGGGCGGGT TCGGTGATCCAGGTGCCTTC-
GAGGGTGGAGAAGAAGGGGACGCGCGGAGCGTG
CGGGGTGAGTCC GGTGAGGACGTCGGC-
GAGCTCGTTCTCGATGGTCTC-
GACGTGGGCGCTGTGGGAGGCGTAGTCGA CGGG-
GATGACCCGCGCGGACCCCGTCCGCCTTGCACG
TACGGGCGAGCTCCTCGATCTGTGCG GGGTCGC-
CCGAAACGACGGTGGCGGTGGGCCCGT-
TGAGGGCGGCGACGGACAGCCCGTCGAGGTT
CTGGATCCGCTCCAGGACGTCGGTCTG-
GCTGAGGGCGAGGGAGATCATGC
CGCCCTTGCCGGCGA GGTGAGCGGCGATGGACCG-
GCTGCGTAGGGCGACGACGCGGGCG-
GCATCCTCCAGGCTCAGTGCC CCGGCGACG-
TACGCGGCGGCGATCTCGCCTTGCGAGTGCCCGAT
GACGGCCTGCGGGGTCACGCC GTGGTGCTGCCA-
GAGCTTGGCCAGCGAGACCATGACGGC-
GAAGGTGACGGGCTGCACCACATCGA CGCGGTC-
GAGCGTGGGGGCGCCGGGTGTCTGCCGGACGACGG
CCTCCAGTGACCA
GTCCACATAC GGCGCGAGCGCGGCCTCGCACTCG-
GCCATCGTCTCCGCGAACTCCTTC-
GACGTGTCGAGGAGTTC GGCTCCCATTCCGGC-
CCACTGCGTGCCCTGGCCGGGGAAGACGAACGCC
ACCCGGCCCACGTCCG TGGACGTTCCCCGTAT-
CAGCCCTTCCGGAGCGGTCAGCGCCTGT-
GCGAAGTCGCCCGTCCCGGTG CCGATCGCGACG-
GCCCGGTGCTCGAACTGCGCGCCCCGTCGGCCAG
TACGCGGGCGACGGCGCC GGCGTCGACGTCATC-
CGTACCGCCCTGCGAGGCGTACGCGGC-
GAGGCGCCCGATCTGGGCGTCCA GCGCGGCCG-
GAGACTTCGCCGAGACCAGCCACGGCACCAGGCCG
CCGGCGGACGGCTCGACGGCC
GGGGTCTCGTTTGTCAGGGTCTCGTC-
CGCCGGGGTCTCGACGACCCCCGGGGCCTCTTCGA
Contig 95 (SEQ ID NO:6)
GGCCCGGCGGCCCTGGACCTCATGGC-
CACCGTCCTCGCCGGCGGTACCGGTGAG-
GACCAGGTCGC CGTGCGCGCCTCCGGGCT-
GCTCGCCCGCCGCCTCGTCCGCGCCGCCCTCCCCG
CTCACGGGACGG CTTCGCCGTGGTGGCAGGC-
CGACGGCACGGTGCTCGTCACCGGTGC-
CGACGAGCCGGCCGCCGCC GAGGCCGCGCGC-
CGCCTGGCCCGCGACGGCGCCGGACACCTCCTCCT
CCACA
CCGGCCCCGTGGC GGGTACGGAGGACTCCGAC-
CCCACCGACCCCACCGACCCCACCGAC-
CCCACCGGCCTCACCGGCC TCGTCGC-
CGAGCTCGCCGACCTCGGCGCGACGGCCACCGTCG
TGTCCTGCGACCTCAC
GGACCGG GAGGCGGCCGCCCGGCTGCTCGCCG-
GCGTCTCCGACGAGCACCCGCTCAGCGC-
CGTCCTCCACCT GCCGCCCACCGTCGACTC-
CGAGCCGCTCGCCGCCACCGACCCGGACGCACTC
GCCCGCGTCGTAA CCGCGAAGGCCACCGC-
CGCGCTGCACCTGGACAGCCTGCTGCGG-
GAGTCCGCGGCGGCCGGACGC CGTGCACCCGTC-
CTCGTCCTCTTCTCCTCGGTCGCCGCGACCTGGGC
GGCGCCGGACAGGGCGC GTACGCCGCCGGTACG-
GCCTTCCTCGACGCCCTCGCCGGTCAG-
CACCGTGCCGAAGGGCCCACCG TGACCTCCGTG-
GCCTGGAGCCCCTGGGAGGGCAGCCGCGTCACCGA
GGGCGCGACCGGGGAGCGG CTGCGCCGCCTCG-
GCCTGCGCCCCTCGCTCCCGCGACG-
GCGCTCACCGCCCTGGACACCGCACT CGGCCACG-
GCGACACGGCCGTCACGATCGCCGACGTCGACTGG
TCGAGCTTC
Contig 115 (SEQ ID NO:7)
ACGTGGGAACACGTCCTGCGTCCCAAG-
GTCGACGCGGCGTTCCTCCTCGAC-
GAGCTGACCTCCAC ACCCGCCCACGACCTGGC-
CGCGTTCGTCATGTTCTCCTCCGCCGCCGCCGTCTT
CGGCGGCGCGG GGCAGGGCGCATACGCCGCCGC-
CAACGCCACCCTCGACGCCCTCGCCTG-
GCGCCGCCGCCGCCGCC GGACTCCCCGCCCTCTC-
CCTCGGCTGGGGCCTCTGGGCAGAGAACAGCAGCA
TGACCGGCGGACT GAGCGACACCGAC-
CGCTCGCGGCTGGCTCGTTCCGGGGC-
GACGCCCATGGACAGCGAGGTGACCC TGTCCCTC-
CTGGACGCGGCCATGCGCCGCGACGACCCGGCGCT
CGTCCCGATCGCCCTGGACGTC GCCGCGCTC-
CGGGCCCAGGAGCGCGACGGCATGCTG-
GCGCCGCTGCTCAGCGGGCTCACCCGCGG
GTCGCGGGCCGGCGGCGCTCCGGTCGGC-
CGCCGCAGGGCCGCCGCCGACGGCACCG-
GCCAGGCGG AGAGGGACCTGGGCGGGCG-
GCTCGCCGCGATGACCCCGGACGACAGGACCGCGC
ACCTGCGGGAC CTCGTCCGTACGCACGTGGCGAC-
CGTCCTGGGACACGGCGCCCCGAGCCGGGTCG
ACCTGGAGCG CGCCTTCCGCGACACCGGTTTC-
GACTCCCTCACCGCCGTCGAGCTCCG-
CAACCGCCTCAACGCCG CCACCGGGCTGCGCCTC-
CCGGCCACGCTCGTCTTCGACCACCCCACTCCGGG
GGAGCTCGCCGGG CACCTGCTCGACGAACTCGC-
CGCCGCCGCAGGCGGGTCCTGGGCGGAT-
GACACCGGGTCCGGCTC TGCTTCCGGCTCCG-
GCTCCGGCTCCGGAGGCGCGGTCTCGGCTGCGGAC
CGGCAGACCGCGGCGG CACTCGCCGAGCTCGAC-
CGGCTGGAAGGCGTACTCGCCGC-
CCTCGCGCCCGCCGCCGGCGGCCGT CCG-
GAGCTCGCCGCCCGGCTCAGGGCGCTGGCCGCGGC
CCTGGGGGACGACGGCGGCGCCGCCAC
CGAACTGGACGAGGCGTCCGACGACGAC-
CTCTTCTCCTTCATCGACAAG-
GAGCTGGGCGAATCCG ACTTCTGACCTGACCT-
GACCCGACCCGACCGGCGCGACAAGCGACATCA
GCACCAGCACCAGCAC CACCCAGCCCCCACACA-
CACGGAACGGACAGGCGAGAACGGGAGC-
CATGGCGAACAACGAAGACA AGCTCCGCGACTAC-
CTCAAGCGCGTTACCGCCGAGCTGCAGCAGAACAC
CCGGCGTCTGCGCGAG ATCGAGGGACGCACGCAC-
GAGCCGGTGGCGATCGTGGGCATGGCCT-
GCCGCCTGCCGGGCGGTGT CGCCTCGCCCGAG-
GACCTGTGGCAGCTGGTGGCCGGGGACGGCGACGC
GATCTCGGAGTTCCCGC AGGACCGCGGCTGG-
GACGTGGAGGGGCTGTACGACCCGGAC-
CCGGACGCGTCCGGGCGTACGTAC TGCCGGTCCG-
GCGGGTTCCTCCACGACGCGGGCGAGTTCGACGCC
GACTTCTTCGGGATCTCGCC GCGCGAGGC-
CCTCGCCATGGACCCGCAGCAGCGGCT-
GTCCCTCACCACCGCGTGGGAGGCGATCG
AGCACGCGGGCATCGACCCGACGAGCCT-
GAAGGGCAGCGGCCTCGGCGTCTTCGTC
Contig 98 (SEQ ID NO:8)

GAGCCCGAGCCGGTGCCCGGCGGCCCGGGCAGCGTCGCCGCCGGCCCCGCCGCGGATCCGGAACC GGAGACGTCGATCGACGACCTCGACGCCGAGGCCCTGATCCGGATGGCTCTCGGCCCGCGGAACG CCTGAGCACCCGCCCCGGCCCGTGGCTGCCCCGGCCCTTGCCCGACTGCGGGCCGGGCCCCGGGC CCGCACACCGCCACGTACCACCCCGCACCACCGCCCCCACACGCCCACAACGCCACCACGAGC GGAAGACCACACCCAGATGACGAGTTCCAACGAGCAGTTGGTGGACGCTCTGCGCGCCTCCCTCA AGGAGAACGAAGAACTCCGGAAAGAGAGCCGTCGCCGGGACGACCGGCGGCAG
GAGCCCATGGCG ATCGTCGGCATGAGCTGTCGGTTCGCGGGCGGCATCCAGTCCCCGAGGACCTCTGGGACGCGGT GGCCGCCGGCAAGGACCTCGTATCCGACGTACCTGAGGAGCGCGGCTGGGACTTCGACTCCCTGT ACGACCCGGAGCCCGGGCGGAAGGGCACGACGTACGTCCGCAACGCCGCGTTCCTCGACGACGCC GCCGGCTTCGACGCCGCGTTCTTCGGGATCTCGCCGCGCGAGGCCCTCGCCATGGACCCGCAGCA GCGGCAGCTCCTCGAAGCCTCCTGGGAGGTCTTCGAGCGGGCCGGCATCGACCCCGCGTCGGTGC GCGGCACCGATGTCGGCGTGTACGTGGGATGCGGCTACCAGGACTACCGCCGGACATCCGGGTC GCCCCGAGGGGACCGACGGTTACGTCGTCACCGGCAACTCATCCGCCGTGGCCTCCGGGCGCAT CGCGTACTCCCTCGGTCTCGAGGGGCC

Contig 184 (SEQ ID NO:9)
GCTCGGCGAACTCCCCGCGCCGACCCGCCGGCACACCGAGCACCGCGGCCGCCGCGCCCGTCACC GCCGGACGGACGAAACCCCCCACCAACTCGAAGGCGTACGAAGCCGACGG GTCCGGCGCGAGACC CTCCAGGATCTGCCGGTGACCTCCTCGACCACGGCCCGGCGCTGCCCGCCCACGCCCCGGCA CCTCGGCGGCCGCCGCGGCGCCTGCTCGTGCTCCAGCGGGCAGCCCTCCCCGTAGGAGAGGACC TGCTGCGGCACCGGGACGCCGTGGCACCCGGCACCCCGAACTCCGTCGAGCACAGGACGCTCGCC GCCACGGCGTGATCGGCGGTGACCCAGCTGCCCGTCGGGCTGAAGGAGAG
CACGCCCCGGGCGCG CACCCGCTCGTACGCGGGATACGGATCGTCGGCCTGCCCGCGCAGCACGGCGGCGTACGGGTCGC CGTTCGCGGCGTGGATCCAGTGGATGCCGCGGGTCTCCAGGAGGTGGGCACCGAGCTCGGGGTCG GCCACCGCGCTGACGGTGCGGCCCAGCGGAGGCTGCGTGAGCGCCCGCGCCGGGTCGTCGGTCAC CGTGGGTTCTGCCATCGTTTCGCCGCTCCTTCGATCAGTCGGGTCGG GGGCTGCACGACGCGGA ATCGGGCGCGCCGCGGGTGACGAGCAGGTGGTCGGAGATGTCGTTGCAGATCCCGTGCCACTGGT CGTTGAGGTAGAAGTGACCGCCGGAGTACGCCCGCAGGCAGAACGGCCCGCTGGTGTGCCGGCGC CACTCGGCCACCTCGTTCAGCGGCGCCTTCGGGTCGCGGTCGCCGGCCACGGCCATCACCGGGCA GGCGAGCTTCGCGGAGGGCCGGTGCTCGTACGTCTCCGCCGCCTTGTAGTCGCTGCGCAGCGCGG GCAGCCAGCCGCATCAGCTCGTCGTCCTGGAGGAACCGCTCGTCCGTGCCGCTGAGCTGCCGG ATCTCGGCCAGGAACGCCCGGTCGTCCAGCTGGTGGACGAG
CCGGTCCGGTGCCAGGGACGGGGC GCGCCGGCCGGAGACGTACAGGCCCTCGGGCCGTACCCCGTGCCGCTGTTCGAGGATGCGGGCCG CCTCGTA Contig 88 (SEQ ID NO:10)
GGGGACGATCCCCGCCGGGGTGGGGTCGCGATGGGTCTCCTCGCGCAGCCGGTGCGCGGCGGCGA GGACCGAGGGGTCGTCGAGGATGCGGACGACCGCGTCCCGCACCGCCTGCGGGGTGAGGCCGGCA GGCGGCAGGAAGAACCCCGCCCCTGCTCCGCGACGGCCCGCGCCTTGACCGGCGCGTCCCACAG CTCGGCGAGCATGACCTGCGGCACCGCGTTGATCACGGCGGTCGCGTACGTACCG GCCCCGCCGT GGTGGACGATCGCCAACAGCTCGGCAGCAGCGCGTGCATCGGCACGAAGTCCGTGAACCGCGTG TGCTTCGGATAGGAGCGGATCTCCGCGCGCTGACCCGCGTCGAGCGTGGCCACGAGCTCGATGTC GAGGTCGGCGAGCGCCTCCAGGATGTCGGCCTGCGAGACCCCGTCGCCGCCGAGGACCTCCCGCG CGGAGACACCGAGAGTGAGGCAGACCCGGGGCCGCCGGCGGCTCGGCGAGCCAGTCCGGCACG ACCGACGTGCCGTTGTACGGAACGTACTGCACCCCGACGGTCGGCAGACCCGTGTCGAGACGCAG ACTCGGCGGAGTCGGGTCGACCGTGAACTGGCCGGTGAGCAGCTCCTCTTCGA
AGGAGGCGCCGA ACCGGTCCAGCGTCCACGTCAGCCACTCCGCCGTGGGGTCCTCACGGTGCTCCGGCGGCTGCCGG TCCCGCAGCGCGACGAACTTGCGGCGGGCGCTCCCCATCACGTCGGGCCCCCACAGGACCCGGGC GTGCGCGGCGCCCGTGACCTGGGCGGCGACGGCGCCGCGTACGTCGTCGGCTCCCACAGCACCA GGTCCGGCTGCCAGGACCTGGCGAAGCCGACCAGGTCGTCGATCATCGAGTCGTTGTTGGCGAGC AGATAGAAGTACGGGGCGAGGATCGCGTCGATGCCGAGGGCGTGGTCCCAGTCCAGCGGCTCGCT ACGGGCCTCGTCGAAGGCGATCGCCGGATGGTTCGGGCGCGGCTCGCCCGC
CATCCGCACCCGGT ACTCGTGGATGAGGTGATCCGTGCCGACGGGCACGGCCGCGAGCCCTGACCCGGTGATGGTGTCC GTGAGCGGGCTGGCTCGCGACCCGCACCTCGTGCCCGGCGGCGAGCAGCGCCCAGGCCAGGGG AACGAGGCCGTAGTAGTGCGTGTGATGTGCGAACGAGGTCAGCAGGACGCGCATGGCGTCGTGTC CTTCCTTGCCGGTGAAGGGTCGGGGTGGGGAGGCGGGGTGGGGAGGTCGGAACGGACTCAGGAGC CGACCGGGACGCTCAGCGGCCCGCGGCCGACAGGGGCGCGGCGGGGACGGAGCACGGGCCCGCC TTCCGCAGCCCGGGGAAACGCCCGGCCAGGGTCCGCAGCGCGACCTCCGCCTGGAGCCGCACCAG CGACGCCACCGGGCCGTACGGACCGGCGGGGTGCAGCGCGAGGTGCGCCGTGGCGTCGGGGCGCG CGAGGTCGAAACGCTCCGGGTCCGTGAAGACCCCCGGGTCCCGGCCGGTGCCGGCGTGAGGACG ACGACATGCGCCCGGCCGGAGACGCCGGCCCGCCAGCT Contig 93 (SEQ ID NO:11)
GCAGGAGTCCCGTGTACGAAGTCGACCACGCCGACGTCTACGACCTCTTCTACCTCGGTCGCGGC AAGGACTACGCCGCCGAGGCCTCCGACATCGCCGACCTGGTGCGGACCCGTACCCCCGAGGCCTC CTCGCTCCTGGACGTGGCCTGCGGTACGGGCACGCATCTGGAGCACTTCACCAAGGAGTTCGGCG ACACCGCGGCCTGGAGCTGTCCGAGGACATGCTGACCCACGCCCGGAAGCGGCTGCCCGACGCG ACGCTCCACCAGGGCGACATGCGGGACTTCCGCCTCGGCCGCCGGTTCTCCGCGGTGGTCAGCAT GTTCAGCTCCGTCG GCTACCTGCGGACGACGGCCGAACTCGACGCGGCC
GTCGCCTCGTTCGCCG CGCACCTGGAGCCCGGCG-
GCGTCGTCGTCGTCGAGCCGTGGTGGT-
TCCCGGAGACCTTCGCCGAC GGCTGGGTGAGCGC-
CGATGTCGTCCGGCGGGACGGGCGGACCGTGGCCC
GTGTCTCGCACTCGGT GCGGGACGGCGACGC-
GACGCGCATGGAGGTGCACTTCACCGTG-
GCGGACCCGGGCCGCGGCGTAC GGCACTTCTC-
CGACGTCCACCTCATCACCCTGTTCCACCGGGCGGA
GTACGAGGCGGCCTTCACG GCCGCCGGGCT-
GCGCGTCGAGTACCTGGAGGGCGGC-
CCGTCGGGCCGTGGCCTCTTCGTCGGGGT
CCCCGCCTAGTCCCTCGCCCGGTCAC-
CCCACACAGACCCCCGGGGCGTCCCGGGTGC
ACCAAGCA CAGAGAGAGAAATCCACCGTGACAG-
GTAAGACCCGAATACCGCGTGTCCGCCG-
CAGCCGTACGAC CCCCAGGGCCTTCACCCTGGC-
CGTCGTCGGCACCCTGCTGGCGGGCACCACCGTGG
CGGCCGCCG CTCCCGGCGCCGCCGGCACGGGC-
CACGTGCAGTACACGAGCAAGGCGGCG-
GAGCTCGTCGCGCAG ATGACGCTCGACGAGAA-
GATCAGCTTCGTCCACTGGGCGCTGGACCCCGACC
GGCAGAACGTCGG CTACCTTCCGGGCGTGC-
CGCGTCTCGGCATCCCGGAGCTGCGCGC-
CGCCGACGGCCCGAACGGCA TCCGTCTG-
GTGGGCAGGACGCCACCGCGCTGCCCGCGCCGGT
CGCCCTGGCCAGCACCTTCGAC GACTCCATGGC-
CGACAGCTACGGCAGGGTCATGGGCCGC-
GACGGACGCGCGCTGGGCCAGGACAT GGT-
TCTGGGCCCGATGATGAACAACATCCGGGTGCCACA
CGGCGGCCGGAACTACGAGACCTTCA GCGAG-
GACCCCCTGGTCTCCTCGCGCACCGCG-
GTCGCCCAGATCAAGGGCATCCAGGGTGCGGGT
CTGATGACCACGGCCAAGCACTTCGCG-
GCCAACAACCAGGAGA
ACAACCGCTTCAGCGTCAACGC CACGGTCGAC-
GAGCAGACGCTCCGCGAGATCGAGTTC-
CCGGCGTTCGAGGCGTCCTCGAAGGCCG GCGCG-
GCCTCCTTCATGTGTGCCTATAACGGCGTCAACGGC
AAGCCGTCCTGCGGCAACGACGAG CTGCTCAA-
CAACGTGCTGCGCACGCAGTGGGGCTTC-
CAGGGCTGGGTGATGTCCGACTGGCTCGC CAC-
CCCGGGCACGGACGCCATCACCAAGGGCCTCGACC
AGGAGATGGGCGTCGAGCTCCCCGGCG ACATC-
CCGCCGGGCGAGCCCTCGCCGCCGGC-
CAAGTTCTTCGGTGACGCGCTGAAGCAGGCCGTC
CTGAACGGCACGGTCCCCGAGGCGGC-
CGTGACGCGGTCGGCG
GAGCGCATCGTCAACCAGATGGA CAAGTTCG-
GTCTGCTCCTCGCGACTCCGGCGC-
CCCGCCCCGAGCGTGACAAGGCGGGCGCCCAGG
CGGTGTCCCGCAAGGTCGCCGAGAACG-
GCGCGGTGCTCC
TGCGCAACGAGGGCCAGGCCCTGCCG CTCGCCG-
GTGACGCCGGCAAGAGCATCGCCGT-
CATCGGCCCGACGGCCGTCGACCCCAAGGTCAC
CGGCCTGGGCAGCGCCCACGTCGTCCCG-
GACTCGGCGGCGGCGCCGCTCG
ACACCATCAAGGCCC GCGCGGGGCGCGGGTGC-
GACGGTGACGTACGAGACGGGTGAG-
GAGACCTTCGGGACGCGGATCCCG GCGGCG-
CAGCTCAGCCCGGCGTTCAACCAGGGCCACCAGCT
GGAGCCGGGCAAGGCGGGGCGCT GTACGACG-
GCACGCTGACCGTGCCCGCCGACGGC-
GAGTACCGCATCTCGGTCAAGGCCACCGGTG
GCTACGCGACGGTGCAGCTCGGCAGCCA-
CACCATCGAGGCCGGTCAGGT CTACGGCAAGGTGAGC AGCCCGCTCCTCAAGCT-
GACCAAGGGCACGCACAAGCTCAC-
GATCTCGGGCTTCGCGATGAGCGC CACGC-
CGCTCTCCCTGGAGCTGGGCTGGGTGACGCCGGAG
GCAGCCGACGCGACGATCGCGAAGG CCGTG-
GAGTCGGCGCGGAAGGCCCGTACGGC-
CATCGTGTTCGCGTACGACGACGGCACCGAGGGC
GTCGACCGTCCGAACCTGTCGCTGC-
CGGGTACGCAGGACAAGCTGATCTCGG
CGGTCGCCGACGC GAACCCGAACACGATCGTG-
GTCCTCAACACCGGTTCGTCGGTGCT-
GATGCCGTGGCTGTCCAAGA CCCGCGCGGTCCTG-
GACATGTGGTACCCGGGCCAGGCGGGCGCCGAGGC
GACCGCCGCGCTGCTC TACGGTGACGTGAAC-
CCGAGCGGCAAGCTCACGCAGAGCTTC-
CCGGCCGCCGAGAACCAGCACGC CGTCGCCGGC-
GACCCGAACCGCTACCCGGGCGTCGACAACCAGCA
GACGTACAGCGAGGGCATCC ACGTCGGGTAC-
CGCTGGTTCGACAAGGAGAACGTCAAGC-
CGCTGTTCCCGTTCGGGCACGGCCTG TCGTACAC-
CTCGTTCACGCAGAGCGCCCCGACCGTGGTGCGCA
CGTCCACGGGCGGCCTGAAGGT CACGGTCACGGT-
GCGCAACAGCGGGCAGCGCGCGGGCCAG-
GAGGTCGTCCAGGCGTATCTCGGCG CGAGC-
CCGAAGGTGACGGCTCCGCAGGCGGAGAAGAAGC
TCGTGGGCTACACGAAGGTCGCGCTC GCG-
GCGGGCGAGTCGAAGACGGTGACGGT-
GAACGTCGACCGCCGTCAGCTGCAG-
TACTGGGACGC
CGCGTCGGACTCGTGGAGGACGG-
GAACGGGCAGCAGGCTCCTCCAGACCGGTTCGT
Contig 122 (SEQ ID NO:12)
GGGGGTGATCGCCTTCTCGACGAG-
CAGCGGGTCGAGGGTGGGGTGGTC-
CTCGTTCGGCTCGACGG GCACGGGGGTCGCGCCG-
GTGGCGGAGACCGCGAGCCAGCTGGCGATGTACGT
GTGCGAGGGGACG ATCACCTCGTCCCGGGTC-
CGATGCCGAGGCCGCGGAGCGCGAGCTG-
GAGGGCGTCCATGCCGCT GTTCACGCCGACG-
GCGTGGTCGGTCTCGCAGTAGGTGGCGAACTCGGC
TTCGAAGGCTTCGAGTT CGGGGCCGAGGAGG-
TAGCGCCCCGAGTCGAGTACGCGGGC-
GATGGCGGCGTCGGTCTCCGGGCGC AGTTCCTCG-
TAGGCGGCCTTGAGGTCGAGGAAGGGGACCCGGCC
GGTCTCGGTGCGGCGGTCAC GCGGACAC-
CCCCACGGCGGTGGCGGGCGGCT-
GCGGGGCGGTGGCGGGCGGCTGCGGGGCGGTGGC
CTTGAGCGGTTCCCACCAGTCGCGGT-
TCTCCCGGTACCAGCGGATGGTGCG
CGCGAGGCCGTCCG CGAAGGCGATCTGCGGGCG-
GTAGCCGAGTTCGCGCTCGATCTTGC-
CGCCGTCGAGGGAGTAGCGC AGGTCGTGGCCCTG-
GCGGTCGGCGACCCGCCGGACCGAGGACCAGTCG
GCGCCGAGCGAGTCCAG GAGGATGCCGGTGAGT-
TCGCGGTTGGTCAGCTCCCGGCCGCCGC-
CGATGTGGTAGACCTCGCCGG CCCGGCCGCCCGC-
GAGGACGAGCGCGATGCCCCGGCAGTGGTCGTCGG
TGTGGACCCACTCGCGG ACGTTCGCGCCGTCGC-
CGTACAGCGGGAGCGTCCCGCCGTCGAG-
GAGGTTCGTCACGAAGAGGGG GATGAGCT-
TCTCGGGGTGCTGGTACGGCCCGTAGTTGTTGCAGC
AGCGGGTGATCCGTACGTCGA GGCCGTAGGTGCG-
GTGGTAGGCGCGGGCGACGAGGTCG-
GAGCCGGCCTTGGAGGCCGCGTAGGGG GAGT-
TGGGTTCCAGCGGGCTGCTCTCGTTCCACGAGCCG
GAGTCGATCGACCCGTACACCTCGTC GGTG-
GAGACGTGCACGACCCGGCCGACGCCG-
GCGTCGAGGGCGCACTGGAGCAGGGTCTGCGTGC CCTGGACGTTGGTCCCGGTGAACACG-GACGCCCCGCGATGGAGCGGTCGACGT GGCTCTCGGCG GCGAAGTGGACGACGGCGTC-GACGCCGCGCAGTTCCCGGGCGAGGAG-GTCGGCGTCGCGGATGTC GCCGTGGACGAACCG-CAGCCGCGGGTCCGCTTCCACCGGGGCGAGGTTGG CGCGGTTGCCCGCGT AGGTGAGGCTGTCCAGGAC-GATCACCTCACCGGCGGGGACGTCGGGG-TACGCCCCGGCGAGGAGC TGCCGCACGAAGTGC-GAGCCGATGAAGCCCGCACCTCCGGTCACCAGAA CCGCACTGCCGTCTT CCTTTCGGTCGCGCTGTCG-GTGGCACTGCCGGTGGTGGGGGGAACG Sequence information generated from cosmids of the invention can be used to generate additional nucleic acids of the invention as well as to generate additional sequence information regarding the narbonolide PKS enzyme and narbomycin modification enzymes.

The invention having now been described by way of written description and example, those of skill in the art will recognize that the invention can be practiced in a variety of embodiments, that the foregoing description and example is for purposes of illustration and not limitation of the following claims.

What is claimed is:

1. An isolated nucleic acid that comprises a sequence identical or complementary to all or part of a coding sequence for a narbonolide polyketide synthase gene from *Streptomyces narbonensis*, wherein said, part of said coding sequence is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

2. The isolated nucleic acid of claim 1, wherein said coding sequence encodes a ketosynthase domain.

3. The isolated nucleic acid of claim 1, wherein said coding sequence encodes an acyltransferase domain.

4. The isolated nucleic acid of claim 1, wherein said coding sequence encodes an acyl carrier protein domain.

5. The isolated nucleic acid of claim 1, that encodes a module, said module comprising a ketosynthase domain, an acyltransferase domain, and an acyl carrier protein domain.

6. The isolated nucleic acid of claim 1 that encodes an open reading frame, said open reading frame comprising two or more modules, each module comprising a ketosynthase domain, an acyltransferase domain, and an acyl carrier protein domain.

7. The isolated nucleic acid of claim 1 that encodes a gene cluster, said gene cluster comprising two or more open reading frames, each of said open reading frames comprising two or more modules, each of said modules comprising a ketosynthase domain, an acyltransferase domain, and an acyl carrier protein activity domain.

8. The isolated nucleic acid of claim 1 that is selected from the group consisting of cosmids pKOS037-23 and pKOS037-26.

9. A recombinant DNA expression vector comprising the nucleic acid of claim 8.

* * * * *

SEQUENCE LISTING

<160> NUMBER OF SEQ ID NOS: 12

<210> SEQ ID NO 1
<211> LENGTH: 1590
<212> TYPE: DNA
<213> ORGANISM: Streptomyces narbonensis

<400> SEQUENCE: 1 acagggata tcccgctcca ggcgaacggt agccgcgtgc cctcgccgaa cgccccgccc      60
gcaccggccg cctgcacggc ggcgtcgagc agcgccgggt ggaggccgaa ccgcgcgccc     120
tcggcgcccg cgacctccgt cggcaggcc acgtcggcga acacctcttc gccgcgccgc     180
cagacgccac ggacgccccg gaagaggggc ccgtagccgt atccgctcgc cgcgaagcgg     240
tcgtacagac cgtccacgtc cactgcttcg gcacccgccg ggggccaggc ctccgggtcg     300
gcgacagggg cggtgcgatc cgtacgggcg agcacaccgg tcgcgtgccg cgtccactcc     360
ggctcgcccg gcgcgtcctc cgggtgcgcg tggagcacga aggtacggcg cccggactcg     420
tcgctcgcgc cgacggacag ctgcacgcgg accgcgccgc gacggggcag gacgagcggg     480
gcgtcgaggg tgagctcctc gaccagatcg cagccgacct ggtcaccggc ccggaaggcc     540
agctccacga acgccgttcc cggcagcagc accgtgccgg ccaccgcgtg gtccgccagc     600 cagggtgcg tacggaggga gaggctcccc gtgagcaggc agccgtcgga gtcggcgagc     660
gcgacggccg cgccgagcag cgggtgctcg gccgcccga gaccggcgga cgtgatgtca     720 ccgacggcg agtgctcggg ccgcggccag tagcgctcgg tctggaaggc gtaggtgggg     780
aggtcgggga ggtcggcgtt cgtcgcgttc ttcgtggtcg tggtggggag gacgggtgtc     840
cagtcgaggg ggaggccgtt ggtccaggcc tcggcgagcg aggtgaccag acgctcctgg     900
ccgccgtcct cgcggcggag ggtgccgagg ccggtgacgg tgtcggggag ggccatggtg     960 aggacgggt gggcgctgac ctcgacgaag tgggtgaacc cttcgtcggt ggcgagggtt    1020
tcgacggcgg gggcgaagcc gacggggtgg cggaggttgc ggtaccagta cgtggcgtcg    1080
agggcgggtt cggtgatcca ggcaccgtcg agcgtggaga agaagggac gcgcggagcg    1140 tgcggggtga gtccggcgag gacgtcggcg agctcgttct cgatggtctc gacgtgggcg    1200
ctgtgggagg cgtagtcgac ggggatgatc cgcgcgcgga tgccgtcggc cttgcaggtc    1260
ttcgcgagct cttcgatctg tgcggggtcg ccggagacca cggtggcggt ggggccgttg    1320
acggcggcga tcgacagtcc gtcgagggtg tcgatccgct ccaggacgtc ggcctggctg    1380
agggcgaggg agaccatgcc gccctgccg gcgaggtgag cggcgatgga ccggctgcgt    1440
agggcgacga cgcggcggc atcctccagg ctcagtgccc cggcgacgta cgcggcggcg    1500
atctcgccct gggagtggcc gatgacggcc tgggggtga tgccgtggtg ctgccagatc    1560

```
ttcgcgaggg agaccatgac ggcgaaggtg                                    1590

<210> SEQ ID NO 2
<211> LENGTH: 1419
<212> TYPE: DNA
<213> ORGANISM: Streptomyces narbonensis

<400> SEQUENCE: 2
cgggctggac gacgtcgacg cggtcgagcg tcgggcgcc gggagcctgt cgtacgacgg      60
cttcgaggga ccagtcgacg tgacgggaga gcgcggtctc gcacgcggcc atctccgccg    120
cgaactccgc agaggagtcc agcagttcgg cacccatccc ggaccactgc gtgccctggc    180
cggggaacac gaacgccacg cgcccgacag cggaagccgt gccacgaatc agcccgtccg    240
ggtcggccag ggcctgtacg aggtcgcccg ccccggtgcc cagcgcgacg gcccggtgct    300
cgaactgcgc ccgcccgtcg gccagtacgc gggcgacggc gccggcgtcg acgtcatccg    360
tacgcccctg agaggcgtac gcggcgagcc gctcgatctg ggcgtcgagt gcaccggcgg    420
acttcgccga caccacccac ggcaccacgc cacccgacga cggctcgtcc acggcggtgt    480
tttccaccgt cggggcctct cgaggacga cgtgagcgtt cgtcccgctg atgccgaagg     540
aggagacggg ggcgcggcgc agcccgccgt cctgcttctc cggccagtcc acggcctcgg    600
tgaggagttc cacggcaccg ccgaccagt cgatctggtc cgaggggcg tccacgtgaa      660
gcgtcttcgg gagtagcccg tggcgcatcg cctggaccat cttgatgaca ccggcgacac    720
cggccgcggc ctgggtgtgc ccgatgttgg acttcaacga tccgagcagc aacggacgtt    780
cgccgccccg gtcctgcccg taggtggcga tcagggcctg cgcctcgatc gggtcgccga    840
gccgcgtccc cgtgccgtgc gcctcgacga catcgacctc gcccggcgtg agccgggcgt    900
cggccagggc ccgccggatg acgcgctgct gcgacggccc gttcggagcc gtgagaccgt    960
tgctggcgcc gtcctggttc acggcgctgc cgcggacgac cgcgaggacc cggtgtccgt   1020
ggcggcgggt gtccgacagg cgctcgacga ggaggacacc gacaccctcg gaccaactgg   1080
tgccgtccgc cgacgcggcg aacgccttcg accaccgtc cccggccagc ccgcgctgcc    1140
ggctgaactc cacgaacatc cccggcgtgg gcatcacggc cacgccgccg gcgagcgcca   1200
tgtcgacctc gcccttgcgc agggcctgca cggcgaggtg cagggcgacc agcgacgacg   1260
agcaggcggt gtccaccgtc agggcggggc cctcaaggcc gagcgtgtac gagacgcggc   1320
ccgacatcac gctggccgtg ttgccggtca gcaggtatcc gtcgaggccc tccccgccgt   1380
cgcgcaggct cggcccgtac tcgtgggtca tcgccccgg                           1419

<210> SEQ ID NO 3
<211> LENGTH: 1434
<212> TYPE: DNA
<213> ORGANISM: Streptomyces narbonensis

<400> SEQUENCE: 3
gaacccgtcg gcgtccgccg agaaggcctt gctccggccg tccggggcga gcgcccgctg     60
ccggctgaac tccacgaaca tgtgcggggt cgccatcatc gccacaccac ggcgagtgc     120
catcgagcat tcaccgctcc gcagcgcccg caccgccagg tgcagggcgg tcagcgagga   180
cgagcaggcg gtgtcgacgg tcgtcgcggg cccttcgaga ccgaaggtgt acgcgatgcg   240
gccggacgcg acgctcggcg tgctgccggt cagcaggtaa ccctccacgc gcgcgggggc   300
gttcgggacg cgggccgcgt agtcctggta ggagaggccg atgaagacac cggtgctgct   360
```

-continued

```
gccgcgcagc gagcccggct cgatgccggc ccgctcgaac gcctcccagg acgtcgccag      420
gagcatccgc tgctgcgggt ccatggcgag cgcctcgcgc ggcgagacac cgaagaactc      480
cgcgtcgaac tcggccgcgt cgtgcaggaa cccgccctcg cggacgtacg ccttgccgag      540
cgcgtccggg tcggcgtcgt acaggccgtc gaggtcccag cccggtcgg tggggaaggg       600 cgtgatgccc tcgccgccct cggccagcat ccgccacagg tcctcagggc tgcggatgcc      660
accggggtat cggcagctca tggcgacgat cgcgatcgga tcgtcgtcga caccgagacc      720
gacaccgaga ccgagaccga caccgagacc gacaccggat ccgccaccga caccggatcc      780
gccaccgaga ccagcaccag ctccgccacc gagaccagca ccagctccgg caccgagacc      840
agcgccgaca gcccgcgtcc ccctggccca cgtggactcc gccgccgcgt cctcgtcacc      900
gaggaactcg gcacggagca gtgacgcgag ggccagcggc gtcgggtggt cgaagacgag      960
cgtcgcgggc aaggggagcc cggtcgcccg ggtcagccgg ttgcggagct cgactccggc     1020
gagcgagtcg aagccgatgt ccttgaaggc ccggtcggcg cgacgtcct caggtgaacg      1080 catccggagc acggcggcgg cctgggcccg tacgagaccg aggaggatct ccgtacgctc     1140
gccgggagcc gcggcggcca gccgctcggc cagcgggttc ccgcccgcgg cggagctgcc     1200
gcccggcccg gccggggcgc tctcccgcgc gtcgatgatg cgccgcacct cgggcagctc     1260
ctcgacgagg ggctgagggc ggccgaggga gtacgcgagg tagaaacggt cccagtcgat     1320
gtccgcgacg gtgatcgcgg tctcgtcccg gccgagggcg gactccagtg cggtcagggc     1380
gagttccggg tccatgccgg gtacgccgtg atcgcgcagg cgctcggcca cccc           1434
```

<210> SEQ ID NO 4
<211> LENGTH: 1462
<212> TYPE: DNA
<213> ORGANISM: Streptomyces narbonensis

<400> SEQUENCE: 4

```
agcgggccag gccggagccg gggaccggga ccgggacgtg tccacgccgt ccaggagcac       60
cgcccacacg gatgccctgc tggcacaact caccaggctg gaaggcgcct tggtgctgac      120
gggcctcccg ggcgccccg ggagcgaaga agtcctggag cacctgcgct cccttcgcgc       180
gatggtcacg ggcgagaccg ggagcgggac cggggccgga agcgggggcg ggggcgcgtc      240
cgcggaatcc gggggcggag accctactac gccgacggg gcgggagtg aggaccgcgc       300 gggagtgccg gacttcatga acgcctcggc cgaggaactc ttcggcctcc tcgacatgga      360
ccccagcacg gactgatccc tgccgcacgg ccgcctcccg ccccgggccc cgtccgagac      420
cccgtcccga acccgtcccg ggcacctcga ctcgaatcac ttcatgcgcg cctcgggcgc      480
ctccaggaac tcaaggggac agcgtgtcca cggtgaacga agagaagtac ctcgactacc      540
tgcgtcgcgc cacggcggac ctccacgagg cccgcgccg cctccgcgag ctggaggcca      600
gggcgggcga gccggtggcg atcgtcggca tggcctgccg cctgccgggc ggtgtcgcct      660
cgccggagga cctgtggcgg cttgtggccg gtggcgagga cgcgatctcg gagttcccgc      720
aggaccgcgg ctgggacgtg gagggctgt acgacccgaa cccggaggcc acgggcagga      780
gttacgcccg tgaggccgga ttcctgtacg aggcgggcga gttcgacgcc gacttcttcg      840
ggatctcgcc gcgcgaggcc ctcgccatgg acccgcagca gcggctcctc ctggaggcct      900
cctgggaggc gttcgagcac gccggcatcc cggcggccag tgcgcgcggc acgtcggtcg      960
gcgtcttcac cggcgtgatg taccacgact acgcgacccg tctcaccgac gtccccgagg     1020
gcatcgaggg ctacctgggc accgggaact ccggcagcgt cgcctcgggc cgggtcgcct     1080
```

```
acacgctggg cctggagggc ccggccgtca cggtcgacac ggcctgctcg tcctcgctcg    1140
tcgccctgca cctcgccgtg caggccctgc gcaagggcga ggtcgacatg gcgctcgccg    1200
gcggcgtgac ggtcatgtcg actcccagca ccttcgtcga gttcagccgc cagcgcggac    1260
tggcccccga cggccggtcg aagtccttct cgtcgacggc ggacggcacc agctggtccg    1320
agggcgtcgg cgtcctcctc gtcgagcgcc tgtcggacgc ccgtcgcaag ggccaccggg    1380
tgctcgccgt ggtccggggc acggccgtca accaggacgg cgcgagcagc ggcctcaccg    1440
ccccgaacgg cccgtctcag ca                                             1462
```

<210> SEQ ID NO 5
<211> LENGTH: 1881
<212> TYPE: DNA
<213> ORGANISM: Streptomyces narbonensis

<400> SEQUENCE: 5

```
ggtgctccag ggcggcgacc ctgcccatgc cccacaccat ggcctgggcg ggggaggaga      60
tgtggtcggc gcggccgacg gacaccgcgc acgggtgac gcaccacagc ggagcggcga     120
caccggcgtc ctccagcgcc tgcaccaggg tgagggtggc gccggtgccc cgggtgaagg     180
gggcggggtg gccggggtgc gcgtcctcgt cccaggcgag cagcgagacg acaccgccga     240
cggctccacc ggccgccgcc agggcttcgc ccagcgcctc cgtgagccgc tgccggtcgc     300
tcggtgcgga cacgtccagc cgtacgggt cggcgcccgc accggacagc gcggcgagca     360
ccggggcggc ctcggaggac cggccctcgg gggcgacgac gagccagcga ccggacaggc     420
cggggctctc ggtgccctcg gcgaccgcga gccgcttcca gtcgacgcgg tagcgccagg     480
agtcctgcac ggagccctgg gcggcggggg agtcgtggag ccagtagtga cggcgctgga     540
aggcgtaggt ggggaggtcg gggaggtcgc cggtcgcggc cggaggacg ggcgcccagt     600 cgacggtgag gccgtgggcc caggcttcgg cgagggaggt gatcaggcgg tcgaggccgc     660
cttgttcgcg gcggagggtg ctgaggcctg tgacggtgtc ggggagggcc atggtgagga     720
cggggtgggc ggagacctcg atgaagtggg tgaagccttc ggttgtggcg agggtttcga     780 tggcggggc gaagccgacg gggtggcgga ggttgcggta ccagtaggtg gcgtcgaggg     840
cgggttcggt gatccaggtg ccttcgaggg tggagaagaa ggggacgcgc ggagcgtgcg     900
gggtgagtcc ggtgaggacg tcggcgagct cgttctcgat ggtctcgacg tgggcgctgt     960
gggaggcgta gtcgacgggg atgacccgcg cgcggacccc gtccgccttg cacgtacggg    1020
cgagctcctc gatctgtgcg gggtcgcccg aaacgacggt ggcggtgggc ccgttgaggg    1080
cggcgacgga cagcccgtcg aggttctgga tccgctccag gacgtcggtc tggctgaggg    1140
cgagggagat catgccgccc ttgccggcga ggtgagcggc gatggaccgg ctgcgtaggg    1200
cgacgacgcg ggcggcatcc tccaggctca gtgccccggc gacgtacgcg gcggcgatct    1260
cgccttgcga gtgcccgatg acggcctgcg gggtcacgcc gtggtgctgc cagagcttgg    1320
ccagcgagac catgacggcg aaggtgacgg gctgcaccac atcgacgcgg tcgagcgtgg    1380
gggcgccggg tgtctgccgg acgacggcct ccagtgacca gtccacatac ggcgcgagcg    1440
cggcctcgca ctcggccatc gtctccgcga actccttcga cgtgtcgagg agttcggctc    1500
ccattccggc ccactgcgtg ccctggccgg ggaagacgaa cgccacccgg cccacgtccg    1560
tggacgttcc ccgtatcagc ccttccggag cggtcagcgc ctgtgcgaag tcgcccgtcc    1620
cggtgccgat cgcgacggcc cggtgctcga actgcgcgcg cccgtcggcc agtacgcggg    1680
```

-continued

```
cgacggcgcc ggcgtcgacg tcatccgtac cgccctgcga ggcgtacgcg gcgaggcgcc    1740
cgatctgggc gtccagcgcg gccggagact cgccgagac cagccacggc accaggccgc    1800
cggcggacgc ctcgacggcc ggggtctcgt ttgtcagggt ctcgtccgcc ggggtctcga   1860
cgaccccggg ggcctcttcg a                                              1881
```

<210> SEQ ID NO 6
<211> LENGTH: 897
<212> TYPE: DNA
<213> ORGANISM: Streptomyces narbonensis

<400> SEQUENCE: 6

```
ggcccggcgg ccctggacct catggccacc gtcctcgccg gcggtaccgg tgaggaccag     60
gtcgccgtgc gcgcctccgg gctgctcgcc cgccgcctcg tccgcgccgc cctcccgct    120 cacgggacgc cttcgccgtg gtggcaggcc gacggcacgg tgctcgtcac cggtgccgac   180
gagccggccc ccgccgaggc cgcgcgccgc ctggcccgcg acggcgccgg acacctcctc   240
ctccacaccg gccccgtggc gggtacggag gactccgacc ccaccgaccc caccgacccc   300 accgaccccca ccggcctcac cggcctcgtc gccgagctcg ccgacctcgg cgcgacggcc   360
accgtcgtgt cctgcgacct cacggaccgg gaggcggccg cccggctgct cgccggcgtc   420
tccgacgagc acccgctcag cgccgtcctc cacctgccgc ccaccgtcga ctccgagccg   480
ctcgccgcca ccgacccgga cgcactcgcc cgcgtcgtaa ccgcgaaggc caccgccgcg   540
ctgcacctgg acagcctgct gcgggagtcc gcggcggccg gacgccgtgc acccgtcctc   600
gtcctcttct cctcggtcgc cgcgacctgg ggcggcgccg gacagggcgc gtacgccgcc   660
ggtacggcct tcctcgacgc cctcgccggt cagcaccgtg ccgaagggcc caccgtgacc   720
tccgtggcct ggagcccctg ggagggcagc cgcgtcaccg agggcgcgac cggggagcgg   780
ctgccgcgcc tcggcctgcg ccccctcgct ccgcgacggg cgctcaccgc cctggacacc   840
gcactcggcc acggcgacac ggccgtcacg atcgccgacg tcgactggtc gagcttc      897
```

<210> SEQ ID NO 7
<211> LENGTH: 1681
<212> TYPE: DNA
<213> ORGANISM: Streptomyces narbonensis

<400> SEQUENCE: 7

```
acgtgggaac acgtcctgcg tcccaaggtc gacgcggcgt tcctcctcga cgagctgacc     60
tccacacccg cccacgacct ggccgcgttc gtcatgttct cctccgccgc cgccgtcttc   120
ggcggcgcgc ggcagggcgc atacgccgcc gccaacgcca cctcgacgc cctcgcctgg   180 cgccgccgcg ccgccggact ccccgccctc tccctcggct ggggcctctg gcagagaac    240 agcagcatga ccgcggact gagcgacacc gaccgctcgc ggctggctcg ttccggggcg    300
acgcccatgg acagcgaggt gaccctgtcc ctcctggacg cggccatgcg ccgcgacgac   360
ccggcgctcg tccgatcgc cctgacgtc gccgcgctcc gggcccagga gcgcgacggc     420
atgctggcgc cgctgctcag cgggctcacc cgcgggtcg gggccggcgg cgctccggtc    480
ggccgccgca gggccgccgc cgacggcacc ggccaggcgg agagggacct gggcgggcgg   540
ctcgccgcga tgacccgga cgacaggacc gcgcacctgc gggacctcgt ccgtacgcac   600
gtggcgaccg tcctgggaca cggcgccccg agccgggtcg acctggagcg cgccttccgc  660
gacaccggtt tcgactccct caccgccgtc gagctccgca accgctcaa cgccgccacc  720 ggctgcgcc tcccggccac gctcgtcttc gaccaccca ctccggggga gctcgccggg   780
```

-continued

```
cacctgctcg acgaactcgc cgccgccgca ggcgggtcct gggcggatga caccgggtcc    840
ggctctgctt ccggctccgg ctccggctcc ggaggcgcgg tctcggctgc ggaccggcag    900
accgcggcg cactcgccga gctcgaccgg ctggaaggcg tactcgccgc cctcgcgccc     960
gccgccggcg gccgtccgga gctcgccgcc cggctcaggg cgctggccgc ggccctgggg   1020
gacgacggcg gcgccgccac cgaactggac gaggcgtccc acgacgacct cttctccttc   1080
atcgacaagg agctgggcga atccgacttc tgacctgacc tgaccccgacc cgaccggcgc   1140
gacaagcgac atcagcacca gcaccagcac cacccagccc cacacacac ggaacggaca    1200
ggcgagaacg ggagccatgg cgaacaacga agacaagctc cgcgactacc tcaagcgcgt   1260
taccgccgag ctgcagcaga acacccgcg tctgcgcgag atcgagggac gcacgcacga    1320
gccggtggcg atcgtgggca tggcctgccg cctgccgggc ggtgtcgcct cgcccgagga   1380
cctgtggcag ctggtggccg gggacggcga cgcgatctcg gagttccgc aggaccgcgg    1440
ctgggacgtg gaggggctgt acgacccgga cccggacgcg tccgggcgta cgtactgccg   1500
gtccggcggg ttcctccacg acgcgggcga gttcgacgcc gacttcttcg ggatctcgcc   1560
gcgcgaggcc ctcgccatgg acccgcagca gcggctgtcc ctcaccaccg cgtgggaggc   1620
gatcgagcac gcgggcatcg acccgacgag cctgaagggc agcggcctcg gcgtcttcgt   1680
c                                                                  1681

<210> SEQ ID NO 8
<211> LENGTH: 872
<212> TYPE: DNA
<213> ORGANISM: Streptomyces narbonensis

<400> SEQUENCE: 8
gagcccgagc cggtgcccgg cggcccgggc agcgtcgccg ccggcccgc cgcggatccg      60
gaaccggaga cgtcgatcga cgacctcgac gccgaggccc tgatccggat ggctctcggc    120
ccgcggaacg cctgagcacc cgccccggcc cgtggctgcc ccggccctttg cccgactgcg    180
ggccgggccc cgggccgca caccgccacg taccaccccg caccaccgcc ccccacacgc     240
ccacaacgcc atccacgagc ggaagaccac acccagatga cgagttccaa cgagcagttg    300
gtggacgctc tgcgcgcctc cctcaaggag aacgaagaac tccggaaaga gagccgtcgc    360
cgggacgacc ggcggcagga gcccatggcg atcgtcggca tgagctgtcg gttcgcgggc    420
ggcatccagt cccccgagga cctctgggac gcggtggccg ccggcaagga cctcgtatcc    480
gacgtacctg aggagcgcgg ctgggacttc gactccctgt acgaccggga gcccgggcgg    540
aagggcacga cgtacgtccg caacgccgcg ttcctcgacg acgccgccgg cttcgacgcc    600
gcgttcttcg ggatctcgcc gcgcgaggcc ctcgccatgg acccgcagca gcggcagctc    660
ctcgaagcct cctgggaggt cttcgagcgg ccggcatcg accccgcgtc ggtgcgcggc     720
accgatgtcg gcgtgtacgt gggatgcggc taccaggact acgcgccgga catccgggtc    780
gccccccgagg ggaccgacgg ttacgtcgtc accggcaact catccgccgt ggcctccggg   840
cgcatcgcgt actccctcgg tctcgagggg cc                                  872

<210> SEQ ID NO 9
<211> LENGTH: 1112
<212> TYPE: DNA
<213> ORGANISM: Streptomyces narbonensis

<400> SEQUENCE: 9
```

-continued

```
gctcggcgaa ctccccgcgc cgacccgccg gcacaccgag caccgcggcc gccgcgcccg      60
tcaccgccgg acggacgaaa ccccccacca actcgaaggc gtacgaagcc gacgggtccg     120
gcgcgagacc ctccaggatc tgccggtgga cctcctcgac cacggcccgg cgctgccccg     180
cccacgcccc cggcacctcg gcggccgccc gcggcgcctg ctcgtgctcc agcgggcagc     240
cctccccgta ggagaggacc tgctgcggca ccggacgcc gtggcacccg gcaccccgaa      300
ctccgtcgag cacaggacgc tcgccgccac ggcgtgatcg gcggtgaccc agctgcccgt     360
cgggctgaag gagagcacgc cccgggcgcg caccgctcg tacgcgggat acggatcgtc      420
ggcctgcccg cgcagcacgg cggcgtacgg gtcgccgttc gcggcgtgga tccagtggat     480
gccgcgggtc tccaggaggt gggcaccgag ctcgggtcg gccaccgcgc tgacggtgcg      540
gcccagcgga ggctgcgtga cgcccgcgc cgggtcgtcg gtcaccgtgg gttctgccat      600
cgtttcgccg ctccttcgat cagtcgggtc ggggctgca cgacgcggga atcgggcgcg      660
ccgcgggtga cgagcaggtg gtcggagatg tcgttgcaga tcccgtgcca ctggtcgttg     720
aggtagaagt gaccgccgga gtacgcccgc aggcagaacg gcccgctggt gtgccggcgc     780
cactcggcca cctcgttcag cggcgccttc gggtcgcggt cgccggccag ggccatcacc     840
gggcaggcga gcttcgcgga gggccggtgc tcgtacgtct ccgccgcctt gtagtcgctg     900
cgcagcgcgg gcagcaccag ccgcatcagc tcgtcgtcct ggaggaaccg ctcgtccgtg     960
ccgctgagct gccggatctc ggccaggaac gcccggtcgt ccagctggtg gacgagccgg    1020
tccggtgcca gggacgggc gcgccggccg gagacgtaca ggccctcggg ccgtaccccg     1080
tgccgctgtt cgaggatgcg ggccgcctcg ta                                  1112
```

<210> SEQ ID NO 10
<211> LENGTH: 1600
<212> TYPE: DNA
<213> ORGANISM: Streptomyces narbonensis

<400> SEQUENCE: 10

```
ggggacgatc cccgccgggg tgggtcgcg atgggtctcc tcgcgcagcc ggtgcgcggc       60
ggcgaggacc gagggtcgt cgaggatgcg gacgaccgcg tcccgcaccg cctgcggggt     120
gaggccggca ggcggcagga agaacccgc cccctgctcc gcgacggccc gcgccttgac     180
cggcgcgtcc cacagctcgg cgagcatgac ctgcggcacc gcgttgatca cggcggtcgc     240
gtacgtaccg gccccgccgt ggtggacgat cgccgaacag ctcggcagca gcgcgtgcat     300
cggcacgaag tccgtgaacc gcgtgtgctt cggataggag cggatctccg cgcgctgacc     360
cgcgtcgagc gtggccacga gctcgatgtc gaggtcggcg agcgcctcca ggatgtcggc     420
ctgcgagacc ccgtcgccgc cgaggacctc ccgcgcggag acaccgagag tgaggcagac     480
ccgggggccgc gccggcggct cggcgagcca gtccggcacg accgacgtgc cgttgtacgg     540
aacgtactgc accccgacgg tcggcagacc cgtgtcgaga cgcagactcg gcggagtcgg     600
gtcgaccgtg aactggccgg tgagcagctc ctcttcgaag gaggcgccga accggtccag     660
cgtccacgtc agccactccg ccgtggggtc ctcacggtgc tccggcggct gccggtcccg     720
cagcgcgacg aacttgcggc gggcgctccc catcacgtcg gcccccacac ggacccgggc     780
gtgcgcggcg cccgtgacct gggcggcgac ggcgcccgcg tacgtcgtcg gctcccacag     840
caccaggtcc ggctgccagg acctggcgaa gccgaccagg tcgtcgatca tcgagtcgtt     900
gttggcgagc agatagaagt acggggcgag gatcgcgtcg atgccgaggg cgtggtccca     960
gtccagcggc tcgctacggg cctcgtcgaa ggcgatcgcc ggatggttcg ggcgcggctc    1020
```

```
gcccgccatc cgcacccggt actcgtggat gaggtgatcc gtgccgacgg gcacggccgc   1080
gagccctgac ccggtgatgg tgtccgtgag cgcgggctgg ctcgcgaccc gcacctcgtg   1140
cccggcggcg agcagcgccc aggccagggg aacgaggccg tagtagtgcg tgtgatgtgc   1200
gaacgaggtc agcaggacgc gcatggcgtc gtgtccttcc ttgccggtga agggtcgggg   1260
tggggaggcg gggtggggag gtcggaacgg actcaggagc cgaccgggac gctcagcggc   1320
ccgcggccga caggggcgcg gcggggacgg agcacgggcc cggccttccg cagcccgggg   1380
aaacgcccgg ccagggtccg cagcgcgacc tccgcctgga gccgcaccag cgacgccacc   1440
gggccgtacg gaccggcggg gtgcagcgcg aggtgcgccg tggcgtcggg gcgcgcgagg   1500
tcgaaacgct ccgggtccgt gaagaccccc gggtcccggc cggtgccggc ggtgaggacg   1560
acgacatgcg ccccggccgg gagacgccgg cccgccagct                        1600
```

<210> SEQ ID NO 11
<211> LENGTH: 3241
<212> TYPE: DNA
<213> ORGANISM: Streptomyces narbonensis

<400> SEQUENCE: 11

```
gcaggagtcc cgtgtacgaa gtcgaccacg ccgacgtcta cgacctcttc tacctcggtc     60
gcggcaagga ctacgccgcc gaggcctccg acatcgccga cctggtgcgg acccgtaccc    120
ccgaggcctc ctcgctcctg gacgtggcct gcggtacggg cacgcatctg gagcacttca    180
ccaaggagtt cggcgacacc gccggcctgg agctgtccga ggacatgctg acccacgccc    240
ggaagcggct gccgacgcg acgctccacc agggcgacat gcgggacttc cgcctcggcc    300
gccggttctc cgcggtggtc agcatgttca gctccgtcgg ctacctgcgg acgacggccg    360
aactcgacgc ggccgtcgcc tcgttcgccg cgcacctgga gcccggcggc gtcgtcgtcg    420
tcgagccgtg gtggttcccg gagaccttcg ccgacggctg ggtgagcgcc gatgtcgtcc    480
ggcgggacgg gcggaccgtg gcccgtgtct cgcactcggt gcgggacggc gacgcgacgc    540
gcatggaggt gcacttcacc gtggcggacc cgggccgcgg cgtacggcac ttctccgacg    600
tccacctcat caccctgttc caccgggcgg agtacgaggc ggccttcacg gccgccgggc    660
tgcgcgtcga gtacctggag ggcggcccgt cgggccgtgg cctcttcgtc ggggtccccg    720
cctagtccct cgcccggtca ccccacacag accccggggg cgtcccgggt gcaccaagca    780
cagagagaga aatccaccgt gacaggtaag acccgaatac cgcgtgtccg ccgcagccgt    840
acgaccccca gggccttcac cctggccgtc gtcggcaccc tgctggcggg caccaccgtg    900
gcggccgccc ctcccggcgc cgccggcacg gccacgtgc agtacacgag caaggcggcg    960
gagctcgtcg cgcagatgac gctcgacgag aagatcagct tcgtccactg ggcgctggac   1020
cccgaccggc agaacgtcgg ctaccttccg ggcgtgccgc gtctcggcat cccggagctg   1080
cgcgccgccg acggcccgaa cggcatccgt ctggtgggca ggaccgccac cgcgctgccc   1140
gcgccggtcg ccctggccag caccttcgac gactccatgg ccgacagcta cggcagggtc   1200
atgggccgcg acggacgcgc gctgggccag gacatggttc tgggcccgat gatgaacaac   1260
atccgggtgc cacacggcgg ccggaactac gagaccttca gcgaggaccc cctggtctcc   1320
tcgcgcaccg cggtcgccca gatcaagggc atccagggtg cgggtctgat gaccacggcc   1380
aagcacttcg cggccaacaa ccaggagaac aaccgcttca gcgtcaacgc cacggtcgac   1440
gagcagacgc tccgcgagat cgagttcccg gcgttcgagg cgtcctcgaa ggccggcgcg   1500
```

-continued

```
gcctccttca tgtgtgccta taacggcgtc aacggcaagc cgtcctgcgg caacgacgag    1560
ctgctcaaca acgtgctgcg cacgcagtgg ggcttccagg gctgggtgat gtccgactgg    1620
ctcgccaccc cgggcacgga cgccatcacc aagggcctcg accaggagat gggcgtcgag    1680
ctccccggcg acatcccgcc gggcgagccc tcgccgccgg ccaagttctt cggtgacgcg    1740
ctgaagcagg ccgtcctgaa cggcacggtc cccgaggcgg ccgtgacgcg gtcggcggag    1800
cgcatcgtca accagatgga caagttcggt ctgctcctcg cgactccggc gccccgcccc    1860
gagcgtgaca aggcgggcgc ccaggcgtg tcccgcaagg tcgccgagaa cggcgcggtg    1920
ctcctgcgca acgagggcca ggccctgccg ctcgccggtg acgccggcaa gagcatcgcc    1980
gtcatcggcc cgacggccgt cgaccccaag gtcaccggcc tgggcagcgc ccacgtcgtc    2040
ccggactcgg cggcggcgcc gctcgacacc atcaaggccc gcgcgggcgc gggtgcgacg    2100
gtgacgtacg agacgggtga ggagaccttc gggacgcgga tcccggcggc gcagctcagc    2160
ccggcgttca ccagggcca ccagctggag ccgggcaagg cggggcgct gtacgacggc    2220 acgctgaccg tgcccgccga cggcgagtac cgcatctcgg tcaaggccac cggtggctac    2280
gcgacggtgc agctcggcag ccacaccatc gaggccggtc aggtctacgg caaggtgagc    2340
agcccgctcc tcaagctgac caagggcacg cacaagctca cgatctcggg cttcgcgatg    2400
agcgccacgc cgctctccct ggagctgggc tgggtgacgc cggaggcagc cgacgcgacg    2460
atcgcgaagg ccgtggagtc ggcgcggaag gcccgtacgg ccatcgtgtt cgcgtacgac    2520
gacggcaccg agggcgtcga ccgtccgaac ctgtcgctgc cgggtacgca ggacaagctg    2580
atctcggcgg tcgccgacgc gaaccccgaac acgatcgtgg tcctcaacac cggttcgtcg    2640
gtgctgatgc cgtggctgtc caagacccgc gcggtcctgg acatgtggta cccgggccag    2700
gcgggcgccg aggcgaccgc cgcgctgctc tacggtgacg tgaacccgag cggcaagctc    2760
acgcagagct tcccggccgc cgagaaccag cacgccgtcg ccggcgaccc gaaccgctac    2820
ccgggcgtcg acaaccagca gacgtacagc gagggcatcc acgtcgggta ccgctggttc    2880
gacaaggaga acgtcaagcc gctgttcccg ttcgggcacg gcctgtcgta cacctcgttc    2940
acgcagagcg ccccgaccgt ggtgcgcacg tccacgggcg gcctgaaggt cacggtcacg    3000
gtgcgcaaca gcgggcagcg cgcgggccag gaggtcgtcc aggcgtatct cggcgcgagc    3060
ccgaaggtga cggctccgca ggcggagaag aagctcgtgg gctacacgaa ggtcgcgctc    3120
gcggcgggcg agtcgaagac ggtgacggtg aacgtcgacc ccgtcagct gcagtactgg    3180 gacgccgcgt cggactcgtg gaggacggga acgggcagca ggctcctcca gaccggttcg    3240
t                                                                    3241
```

<210> SEQ ID NO 12
<211> LENGTH: 1476
<212> TYPE: DNA
<213> ORGANISM: Streptomyces narbonensis

<400> SEQUENCE: 12

```
gggggtgatc gccttctcga cgagcagcgg gtcgagggtg gggtggtcct cgttcggctc     60
gacgggcacg gggtcgcgc cggtggcgga gaccgcgagc cagctggcga tgtacgtgtg    120 cgagggacg atcacctcgt ccccgggtcc gatgccgagg ccgcggagcg cgagctggag    180
ggcgtccatg ccgctgttca cgccgacggc gtggtcggtc tcgcagtagg tggcgaactc    240
ggcttcgaag gcttcgagtt cggggccgag gaggtagcgc cccgagtcga gtacgcgggc    300
gatggcggcg tcggtctccg ggcgcagttc ctcgtaggcg gccttgaggt cgaggaaggg    360
```

-continued

```
gacccggccg gtctcggtgc gggcggtcac gcggacaccc ccacggcggt ggcgggcggc   420
tgcggggcgg tggcgggcgg ctgcggggcg gtggccttga gcggttccca ccagtcgcgg   480
ttctcccggt accagcggat ggtgcgcgcg aggccgtccg cgaaggcgat ctgcgggcgg   540
tagccgagtt cgcgctcgat cttgccgccg tcgagggagt agcgcaggtc gtggccctgg   600
cggtcggcga cccgccggac cgaggaccag tcggcgccga gcgagtccag gaggatgccg   660
gtgagttcgc ggttggtcag ctcccggccg ccgccgatgt ggtagacctc gccggcccgg   720
ccgcccgcga ggacgagcgc gatgccccgg cagtggtcgt cggtgtggac ccactcgcgg   780
acgttcgcgc cgtcgccgta cagcgggagc gtcccgccgt cgaggaggtt cgtcacgaag   840 aggggggatga gcttctcggg gtgctggtac ggcccgtagt tgttgcagca gcgggtgatc   900
cgtacgtcga ggccgtaggt gcggtggtag gcgcgggcga cgaggtcgga gccggccttg   960
gaggccgcgt aggggagtt gggttccagc gggctgctct cgttccacga gccggagtcg  1020
atcgacccgt acacctcgtc ggtggagacg tgcacgaccc ggccgacgcc ggcgtcgagg  1080
gcgcactgga gcagggtctg cgtgccctgg acgttggtcc cggtgaacac ggacgccccc  1140
gcgatggagc ggtcgacgtg gctctcggcg gcgaagtgga cgacggcgtc gacgccgcgc  1200
agttcccggg cgaggaggtc ggcgtcgcgg atgtcgccgt ggacgaaccg cagccgcggg  1260
tccgcttcca ccggggcgag gttggcgcgg ttgcccgcgt aggtgaggct gtccaggacg  1320
atcacctcac cggcggggac gtcggggtac gccccggcga ggagctgccg cacgaagtgc  1380
gagccgatga agcccgcacc tccggtcacc agaagccgca ctgccgtctt cctttcggtc  1440
gcgctgtcgg tggcactgcc ggtggtgggg ggaacg                           1476
```